United States Patent
Kawabata

(10) Patent No.: US 9,850,378 B2
(45) Date of Patent: Dec. 26, 2017

(54) MONOMER COMPOSITION CONTAINING UNSATURATED POLYALKYLENE GLYCOL ETHER-BASED MONOMER, METHOD FOR PRODUCING COMPOSITION THEREOF, POLYMER OBTAINED USING COMPOSITION THEREOF, AND METHOD FOR PRODUCING POLYMER THEREOF

(75) Inventor: Hiroshi Kawabata, Kanagawa (JP)

(73) Assignee: Nippon Shokubai Co., Ltd., Osaka-Shi, Osaka (JP)

( * ) Notice: Subject to any disclaimer, the term of this patent is extended or adjusted under 35 U.S.C. 154(b) by 290 days.

(21) Appl. No.: 13/876,665

(22) PCT Filed: Sep. 22, 2011

(86) PCT No.: PCT/JP2011/071662
§ 371 (c)(1),
(2), (4) Date: Mar. 28, 2013

(87) PCT Pub. No.: WO2012/043395
PCT Pub. Date: Apr. 5, 2012

(65) Prior Publication Data
US 2013/0184420 A1    Jul. 18, 2013

(30) Foreign Application Priority Data
Sep. 30, 2010 (JP) ................. 2010-222236

(51) Int. Cl.
| | | |
|---|---|---|
| C07C 43/15 | (2006.01) |
| C08F 216/14 | (2006.01) |
| C08F 220/04 | (2006.01) |
| C08L 71/02 | (2006.01) |
| C04B 24/26 | (2006.01) |
| C08F 290/06 | (2006.01) |
| C08G 65/26 | (2006.01) |
| C08F 228/02 | (2006.01) |
| C08G 65/30 | (2006.01) |
| C08F 220/06 | (2006.01) |

(52) U.S. Cl.
CPC .......... *C08L 71/02* (2013.01); *C04B 24/2641* (2013.01); *C04B 24/2647* (2013.01); *C07C 43/15* (2013.01); *C08F 216/1416* (2013.01); *C08F 220/04* (2013.01); *C08F 228/02* (2013.01); *C08F 290/062* (2013.01); *C08G 65/2609* (2013.01); *C08G 65/30* (2013.01); *C08F 220/06* (2013.01); *C08L 2205/05* (2013.01)

(58) Field of Classification Search
CPC .. C08F 220/04; C08F 220/06; C08F 290/062; C08F 216/1416; C08F 216/1425; C08L 2205/05; C04B 24/2605; C04B 24/2641; C04B 24/2647; C07C 43/14; C07C 43/15; C07C 43/16
See application file for complete search history.

(56) References Cited

U.S. PATENT DOCUMENTS

| | | | |
|---|---|---|---|
| 6,727,315 B2 | 4/2004 | Yamamoto et al. | |
| 2002/0104462 A1* | 8/2002 | Nagare | 106/819 |
| 2003/0106464 A1 | 6/2003 | Yamashita et al. | |
| 2003/0125492 A1 | 7/2003 | Yamamoto et al. | |
| 2009/0312504 A1 | 12/2009 | Lorenz et al. | |
| 2011/0065847 A1* | 3/2011 | Kawabata et al. | 524/158 |

FOREIGN PATENT DOCUMENTS

| | | | | |
|---|---|---|---|---|
| DE | WO 2005035624 A1 * | 4/2005 | | C08F 290/06 |
| EP | 1103570 A2 | 5/2001 | | |
| EP | 1866259 A1 | 10/2006 | | |
| EP | 2 194 076 A1 | 6/2010 | | |
| JP | 2001-220417 | 8/2001 | | |
| JP | 2002-173593 | 6/2002 | | |
| JP | 2003-147254 | 5/2003 | | |
| JP | 2003-221266 | 8/2003 | | |
| JP | 2007-271987 | 10/2007 | | |
| JP | 2008-050552 | 3/2008 | | |
| JP | 2008050552 A * | 3/2008 | | |
| JP | 2008-106238 | 5/2008 | | |
| JP | 2009-298685 | 12/2009 | | |
| JP | 2010-079265 | 4/2010 | | |
| JP | 2010-189200 | 9/2010 | | |

(Continued)

OTHER PUBLICATIONS

Machine Translation of JP 2008-050552A; Saito et al; Mar. 6, 2008.*
Abstract; WO 2005/035624 A1; Poellmann et al; Apr. 2005.*
Machine translation; WO 2005/035624 A1; Poellmann et al; Apr. 2005.*
Keto-Enol Tautomerism; Wikipedia; 2010.*
International Preliminary Report on Patentability for PCT/JP2011/071662, dated Apr. 11, 2013, and English translation thereof.
International Search Report for PCT/JP2011/071662, dated Dec. 13, 2011.

(Continued)

*Primary Examiner* — Karuna P Reddy
(74) *Attorney, Agent, or Firm* — Dickinson Wright PLLC

(57) ABSTRACT

A monomer composition containing an unsaturated polyalkylene glycol ether-based monomer is provided having excellent stability. The monomer composition contains an unsaturated polyalkylene glycol ether-based monomer represented by the following chemical formula (1):

$$YO(R^1O)_nR^2 \qquad (1)$$

[in the formula, Y represents an alkenyl group having 2 to 7 carbon atoms; $R^1O$ represents one or two or more types of oxyalkylene groups having 2 to 18 carbon atoms; n represents an average addition mole number of oxyalkylene groups and is a number of 5 to 500; and $R^2$ represents a hydrogen atom or a hydrocarbon group having 1 to 30 carbon atoms], an organic acid, and water, and having a pH of 4 to 13.

11 Claims, No Drawings

(56) References Cited

FOREIGN PATENT DOCUMENTS

| | | | |
|---|---|---|---|
| JP | 2010-276859 | 12/2010 | |
| WO | WO 2006/107069 A1 | 10/2006 | |
| WO | 2009/139328 | 11/2009 | |
| WO | WO 2009139328 A1 * | 11/2009 | ............ C08F 259/00 |
| WO | 2009/153203 | 12/2009 | |
| WO | WO 2010/029117 A2 | 3/2010 | |

OTHER PUBLICATIONS

Supplementary European Search Report dated Sep. 11, 2015 that issued in corresponding European Patent Application No. 11828951.1.

Indian Office Action dated Jul. 28, 2017 in corresponding Application No. 890/KOLNP/2013, 5 pages.

* cited by examiner

MONOMER COMPOSITION CONTAINING UNSATURATED POLYALKYLENE GLYCOL ETHER-BASED MONOMER, METHOD FOR PRODUCING COMPOSITION THEREOF, POLYMER OBTAINED USING COMPOSITION THEREOF, AND METHOD FOR PRODUCING POLYMER THEREOF

TECHNICAL FIELD

The present invention relates to a monomer composition containing an unsaturated polyalkylene glycol ether-based monomer, a method for producing the composition, a polymer obtained by using the composition, and a method for producing the polymer.

BACKGROUND ART

A monomer containing unsaturated polyalkylene glycol (herein below, referred to as an "unsaturated polyalkylene glycol-based monomer") is classified into an ether-based monomer having an ether bond (herein below, referred to as an "unsaturated polyalkylene glycol ether-based monomer") and an ester-based monomer having an ester bond (herein below, referred to as an "unsaturated polyalkylene glycol ester-based monomer"). The polymer compound obtained by polymerization of an unsaturated polyalkylene glycol-based monomer is useful as a raw material for producing various polymers, and thus is used in various fields as cement admixture, a pigment dispersing agent, an anti-static agent, a resin hardener, a dispersing agent for gypsum and water slurry, a dispersing agent for coal and water slurry (CWM), and a thickener or the like. For example, the polycarboxylic acid-based copolymer obtained by reaction between an unsaturated polyalkylene glycol ether-based monomer and an unsaturated carboxylic acid-based monomer is widely used as cement admixture, which dehydrates a cement composition by enhancing the fluidity of the composition (see, Patent Documents 1 to 3). Further, the unsaturated polyalkylene glycol-based monomer is advantageously used as an inorganic pigment dispersing agent for a pigment dispersion used for paper coating (Patent Document 4), or as a photo-sensitive resin composition for a photo-sensitive film or a photomask in a field of flat panel display, shadow mask for CRT, printed circuit board, and semiconductor or the like (Patent Documents 5 to 7).

When an unsaturated polyalkylene glycol-based monomer is used as a raw material for preparing a polymer, the corresponding monomer is generally used after it has been produced, transported, and/or stored. For such case, if the unsaturated polyalkylene glycol-based monomer is a solid at room temperature, the corresponding monomer is required to be dissolved by heating, and thus it is inconvenient in terms of handling for production. Further, since the unsaturated polyalkylene glycol-based monomer may undergo a polymerization reaction under heating and produce a gellified product, the heating process is not desirable.

Patent Document 8 discloses a method for storing and/or transporting a polyalkylene glycol ether-based monomer in the form of an aqueous solution. When this method is used, the heating process can be reduced, and thus the polymerization caused by heating is suppressed. According to the method, the base used for producing a monomer is not neutralized. However, for storage for a long period of time, it is preferable to perform neutralization. For such reasons, as a method including neutralization step, Patent Document 9 discloses a method for producing polyalkylene glycol ester including neutralization step. It is disclosed in the document that, when (meth) acrylic acid polyalkylene glycol ester is added with phosphate, heated, and added with water to give an aqueous solution, stable and turbidity-free (meth) acrylic acid polyalkylene glycol ester with excellent color can be obtained.

According to this method, however, in addition to increased amount of a catalyst to be used, when the unsaturated polyalkylene glycol ether-based monomer is stored in aqueous solution state for a long period of time, turbidity or separation is caused, and thus insufficient stability is obtained.

CITATION LIST

Patent Literature

Patent Document 1: Japanese Patent Application Publication No. 2001-220417
Patent Document 2: Japanese Patent Application Laid-Open No. 2008-106238
Patent Document 3: Japanese Patent Application Publication No. 2009-298685
Patent Document 4: Japanese Patent Application Publication No. 2003-147254
Patent Document 5: Japanese Patent Application Publication No. 2007-271987
Patent Document 6: Japanese Patent Application Publication No. 2010-079265
Patent Document 7: Japanese Patent Application Publication No. 2010-276859
Patent Document 8: Japanese Patent Application Publication No. 2002-173593
Patent Document 9: Japanese Patent Application Publication No. 2008-050552

SUMMARY OF INVENTION

Technical Problem

Under the circumstances, object of the invention is to provide a monomer composition containing an unsaturated polyalkylene glycol ether-based monomer which is turbidity-free and stable even when stored for a long period of time regardless of the amount of catalyst, a method for producing the composition, a polymer obtained by using the composition, and a method for producing the polymer.

Another object of the invention is to provide a polymer with stable performance by using the above monomer composition as a raw material for polycarboxylic acid-based polymer.

Still another object of the invention is to provide cement admixture containing the polycarboxylic acid-based polymer.

Solution to Problem

Inventors of the present invention conducted intensive studies to solve the aforementioned problems, and as a result, found that a monomer composition containing an unsaturated polyalkylene glycol ether-based monomer and an organic acid has excellent stability, and completed the invention accordingly.

Specifically, the object mentioned above is accomplished by a monomer composition containing an unsaturated polyalkylene glycol ether-based monomer represented by the following chemical formula (1):

[Chemical formula 1]

$$YO(R^1O)_nR^2 \quad (1)$$

[in the formula, Y represents an alkenyl group having 2 to 7 carbon atoms; $R^1O$ represents one or two or more types of oxyalkylene groups having 2 to 18 carbon atoms; n represents an average addition mole number of oxyalkylene groups and is a number of 5 to 500; and $R^2$ represents a hydrogen atom or a hydrocarbon group having 1 to 30 carbon atoms], an organic acid, and water, and having a pH of 4 to 13.

Advantageous Effects of Invention

According to the invention, a monomer composition containing unsaturated polyalkylene glycol ether-based monomer, which is stable as not showing any turbidity even after storage for a long period of time, can be provided regardless of the amount of catalyst. The monomer composition containing an unsaturated polyalkylene glycol ether-based monomer of the invention is preferably used as a raw material for polymer. Further, the polymer obtained by using the composition can be preferably used for cement admixture.

DESCRIPTION OF EMBODIMENTS

Provided by the invention is the monomer composition containing unsaturated polyalkylene glycol ether-based monomer represented by the formula (1) above (herein below, it may be simply referred to as a "monomer composition"). The monomer composition of the invention is a raw material for producing a polycarboxylic acid-based polymer. The monomer composition of the invention has excellent stability. As such, when the monomer composition is used as a raw material for polymer, the polymer obtained has no quality fluctuation, and therefore it is unlikely to have performance fluctuation even when the polymer is used as cement admixture. As used herein, the expression "excellent stability" means that the solution is free of turbidity, has no separation or precipitation, and is homogeneous. Specifically, the "stability" is evaluated according to the method described in the examples given below, and "homogeneously transparent" indicates the "excellent stability".

Herein below, embodiments of the present invention are described.

The monomer composition of the invention contains an unsaturated polyalkylene glycol ether-based monomer represented by the following chemical formula (1):

[Chemical formula 2]

$$YO(R^1O)_nR^2 \quad (1)$$

[in which, Y represents an alkenyl group having 2 to 7 carbon atoms; $R^1O$ represents one or two or more types of oxyalkylene groups having 2 to 18 carbon atoms; n represents the average addition mole number of oxyalkylene groups and is a number of 5 to 500; and $R^2$ represents a hydrogen atom or a hydrocarbon group having 1 to 30 carbon atoms], an organic acid, and water, and has a pH of 4 to 13.

First, the constitutional components of the monomer composition of the invention are described.

<Constitutional Components of the Monomer Composition>

1. Unsaturated Polyalkylene Glycol Ether-Based Monomer

The monomer composition of the invention contains an unsaturated polyalkylene glycol ether-based monomer.

The unsaturated polyalkylene glycol ether-based monomer used in the invention is represented by the following chemical formula (1).

[Chemical formula 3]

$$YO(R^1O)_nR^2 \quad (1)$$

In the chemical formula (1), Y represents an alkenyl group having 2 to 7 carbon atoms. As used herein, the "alkenyl group" represents a monovalent group represented by the formula $C_nH_{2n-1}$, which is obtained by removing one hydrogen atom from any carbon atom of an alkene. Preferably, Y is an alkenyl group having 2 to 6 carbon atoms, and more preferably an alkenyl group having 2 to 5 carbon atoms.

Examples of Y include a vinyl group ($CH_2$=CH— group), a 1-methyl-vinyl group ($CH_2$=C($CH_3$)— group), a propenyl group ($CH_3CH$=CH— group), a 2-propenyl group (allyl group) ($CH_2$=$CHCH_2$— group), a 2-methyl-2-propenyl group ($CH_2$=C($CH_3$)—$CH_2$— group), a 2-butenyl group ($CH_3CH$=$CHCH_2$— group), a 3-methyl-3-butenyl group ($CH_2$=C($CH_3$)—$CH_2CH_2$— group), a 3-methyl-2-butenyl group (prenyl group) ($CH_3C(CH_3)$=$CHCH_2$— group), a 2-methyl-3-butenyl group ($CH_2$=$CHCH(CH_3)$—$CH_2$— group), a 2-methyl-2-butenyl group ($CH_3CH$=C($CH_3$)—$CH_2$— group), a 1-methyl-2-butenyl group ($CH_3CH$=$CHCH(CH_3)$— group), a hexyl group ($CH_3CH_2CH_2CH_2CH$=$CH_2$— group), a 5-hexyl group ($CH_2$=$CHCH_2CH_2CH_2CH_2$— group), a 3-heptyl group ($CH_3CH_2CH_2CH$=$CHCH_2CH_2$— group), and a 2-cyclohexyl group. Of these, a vinyl group, a 2-propenyl group (allyl group), a 2-methyl-2-propenyl group, a 3-methyl-3-butenyl group, and a 3-methyl-2-butenyl group (prenyl group) are preferable, a 2-methyl-2-propenyl group and a 3-methyl-3-butenyl group are more preferable, and a 3-methyl-3-butenyl group is still more preferable.

In the chemical formula (1), $R^1O$ represents one or two or more types of oxyalkylene groups having 2 to 18 carbon atoms. $R^1O$ is preferably one or two or more types of oxyalkylene groups having 2 to 8 carbon atoms, and more preferably one or two or more types of oxyalkylene groups having 2 to 4 carbon atoms.

Examples of $R^1O$ include an oxyethylene group, an oxypropylene group, an oxybutylene group, and an oxystyrene group. Of these, an oxyethylene group, an oxypropylene group, and an oxybutylene group are preferable. An oxyethylene group and an oxypropylene group are more preferable. Further, depending on specific case, two or more different $R^1O$ structures may be present in a repeating unit represented by $(R^1O)_n$. However, considering easiness for production of a polyoxyalkylene chain or easiness for structure control, the repeating structure represented by $(R^1O)_n$ preferably has repetition of the same AO structures. Further, for a case in which two or more different $R^1O$ structures are present, those different $R^1O$ structures may be present in any form of random addition, block addition, and alternate addition. Further, for ensuring the balance between hydrophilicity and hydrophobicity, it is preferable to contain, as an essential component, an oxyethylene group in an oxyalkylene group. More specifically, it is preferable that 50% by mole or more is an oxyethylene group relative to 100% by mole of the total oxyalkylene group. It is more preferable that 90% by mole or more is an oxyethylene group relative to 100% by mole of the total oxyalkylene group.

In the chemical formula (1), n represents the average addition mole number of oxyalkylene groups and is a number of 5 to 500. Preferably, it is 10 or more, more preferably 20 or more, still more preferably 40 or more, and even still more preferably 50 or more. Further, it is preferably 300 or less, more preferably 200 or less, still more preferably 150 or less, and particularly preferably 125 or less. When the average addition mole number of oxyalkylene groups, i.e., n, is 5 or more, hydrophilicity is surely obtained for the polymer to be prepared so that the dispersion performance can be improved, and therefore it is preferable. When the average addition mole number of oxyalkylene groups, i.e., n, is 500 or less, the reactivity can be surely obtained during the reaction step, and therefore preferable. Further, the expression "the average addition mole number" means the average mole number of oxyalkylene groups that are added per one mole of a compound.

The unsaturated polyalkylene glycol ether-based monomer is preferably a polymer having specific weight average molecular weight. The weight average molecular weight can be obtained as, for example, weight average molecular weight measured by GPC gel permeation chromatography (herein below, referred to as "GPC") using polyethylene glycol standard.

In the chemical formula (1), $R^2$ represents a hydrogen atom or a hydrocarbon group having 1 to 30 carbon atoms. Examples of the hydrocarbon group having 1 to 30 carbon atoms include a substituted or unsubstituted alkyl group having 1 to 30 carbon atoms, a substituted or unsubstituted aryl group having 6 to 30 carbon atoms, and a substituted or unsubstituted aralkyl group having 7 to 30 carbon atoms.

The alkyl group having 1 to 30 carbon atoms may be any one of a linear, branched, or cyclic alkyl group, and preferred examples thereof include a linear, branched, or cyclic alkyl group such as a methyl group, an ethyl group, a n-propyl group, a n-butyl group, a n-pentyl group (amyl group), a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosanyl group, an i-propyl group, a sec-butyl group, an i-butyl group, a t-butyl group, a 1-methylbutyl group, a 1-ethylpropyl group, a 2-methylbutyl group, an i-amyl group, a neopentyl group, a 1,2-dimethylpropyl group, a 1,1-dimethylpropyl group, a t-amyl group, a 1,3-dimethylbutyl group, a 3,3-dimethylbutyl group, a 2-ethylbutyl group, a 2-ethyl-2-methylpropyl group, a 1-methylheptyl group, a 2-ethylhexyl group, a 1,5-dimethylhexyl group, a t-octyl group, a branched nonyl group, a cyclopropyl group, a cyclopropylmethyl group, a cyclobutyl group, a cyclobutylmethyl group, a cyclopentyl group, a cyclohexyl group, a cyclohexylmethyl group, a cycloheptyl group, a cyclooctyl group, a cyclohexylpropyl group, a cyclododecyl group, a norbornyl group (C7), an adamantyl group (C10), and a cyclopentylethyl group. $R^2$ is preferably a hydrogen, a methyl group, an ethyl group, an n-propyl group, an isopropyl group, an n-butyl group, or an isobutyl group, and more preferably a hydrogen, a methyl group, an ethyl group, a n-propyl group, or a n-butyl group. Further, the alkyl group is an alkyl group having 1 to 10 carbon atoms, and an alkyl group having 1 to 8 carbon atoms is more preferable.

In the present invention, the aryl group represented by $R^2$ may or may not have a substituent group. Preferred examples of the aryl group include an aryl group having 6 to 10 carbon atoms.

Examples of the aryl group having 6 to 30 carbon atoms include a phenyl group, an alkylphenyl group, a phenyl group substituted with an alkylphenyl group, and a naphthyl group.

In the present invention, the aralkyl group represented by $R^2$ may or may not have a substituent group. Preferred examples of the aralkyl group include an aralkyl group having 7 to 30 carbon atoms.

Preferred examples of the aralkyl group having 7 to 30 carbon atoms represented by $R^2$ include a benzyl group, a 1-phenylethyl group, a 2-phenylethyl group, a 3-phenylpropyl group, a 4-phenylbutyl group, a styryl group (Ph-CH=CH— group), a cinnamyl group (Ph-CH=CHCH$_2$— group), a 1-benzocyclobutenyl group, and a 1,2,3,4-tetrahydronaphthyl group.

When the group represented by $R^2$ has a substituent group, examples of the substituent group include an alkyl group having 1 to 3 carbon atoms and an aryl group having 6 to 10 carbon atoms.

As the number of carbon atoms in hydrocarbon group of $R^2$ increases, the hydrophobicity increases and dispersion property is lowered. As such, when $R^2$ is a hydrocarbon group, the number of carbon atoms is preferably 1 to 22, more preferably 1 to 18, still more preferably 1 to 12, and particularly preferably 1 to 4.

Examples of the unsaturated polyalkylene glycol ether-based monomer represented by the chemical formula (1) include polyethylene glycol mono(2-methyl-2-propenyl) ether, polyethylene glycol mono(3-methyl-3-butenyl)ether, and polyethylene polypropylene glycol mono(3-methyl-3-butenyl) ether. In the present invention, a compound obtained by adding 5 to 200 mole of alkylene oxide to alkenyl alcohol such as 2-methyl-2-propen-1-ol having 4 carbon atoms and 3-methyl-3-buten-1-ol having 5 carbon atoms can be particularly preferably used.

According to the preferred embodiment of the invention, the monomer composition contains 65 to 99% by weight of an unsaturated polyalkylene glycol ether-based monomer. Preferably, it is contained in an amount of 67 to 98% by weight, more preferably 70 to 95% by weight, still more preferably 75 to 93% by weight, and particularly preferably 80 to 90% by weight. When the unsaturated polyalkylene glycol ether-based monomer is contained in the range of 65 to 99% by weight, it can be easily handled as a raw material for polymer, and therefore it is desirable.

Content of the unsaturated polyalkylene glycol ether-based monomer in the monomer composition of the invention can be measured by separation and quantification by gel permeation chromatography (GPC).

2. Organic Acid

The monomer composition of the invention contains an organic acid.

As for the organic acid used in the invention, hydrocarbons with acidic property can be used. Preferred examples include hydrocarbons having at least one carboxy group or sulfo group. More preferably, it is hydrocarbons having 1 to 10 carbon atoms, which has at least one carboxy group or sulfo group.

As described herein, the expression "hydrocarbons" means a compound consisting of a carbon atom and a hydrogen atom. As described herein, the expression "hydrocarbons having at least one carboxy group or sulfo group" means hydrocarbons having hydrogen substituted with at least one carboxy group or a sulfo group. Examples of the hydrocarbons include an alkane, an alkene, an alkyne, a cycloalkane, and an aromatic hydrocarbon. The hydrocarbons having at least one carboxy group or sulfo group may be substituted with plural carboxy groups and/or sulfo groups, and it may also have a substituent group other than a carboxy group or a sulfo group. Examples of the substituent group in the invention include a carboxy group; a sulfo group; a halogen atom; a hydroxyl group; a nitro group; an amino group; an alkyl group, an alkoxy group, an alkoxycarbonyl group, an acyl group (—OCOR), and a hydroxyalkyloxy group (-O—R—OH) having 1 to 3 carbon atoms; and an aryl group and an aryloxy group having 6 to 10 carbon atoms. In the aforementioned substituent groups, the expression "1 to 3 carbon atoms" indicates the number of carbons in the portion represented by R.

The organic acid in the invention can be preferably represented by the following formula (3A) or (3B).

[Chemical formula 4]

$$R^6—COOH \quad (3A)$$

$$R^6—SO_3H \quad (3B)$$

In the above formulae (3A) and (3B), $R^6$ represents a substituted or unsubstituted alkyl group, an alkenyl group, an aryl group, or an aralkyl group.

The organic acid used in the invention is preferably non-polymerizable. Accordingly, in the present invention, $R^6$ preferably represents a substituted or unsubstituted alkyl group having 1 to 10 carbon atoms, a substituted or unsubstituted aryl group having 6 to 10 carbon atoms, or a substituted or unsubstituted aralkyl group having 7 to 10 carbon atoms.

In the invention, the alkyl group represented by $R^6$ may or may not have a substituent group. Examples of the alkyl group include an alkyl group having 1 to 10 carbon atoms, and an alkyl group having 1 to 8 carbon atoms is more preferable.

The alkyl group having 1 to 10 carbon atoms can be any of a linear, a branched, or a cyclic alkyl group, and preferred examples thereof include a linear, a branched, or a cyclic hydrocarbon group such as a methyl group, an ethyl group, a n-propyl group, a n-butyl group, a n-pentyl group (amyl group), a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosanyl group, an i-propyl group, a sec-butyl group, an i-butyl group, a t-butyl group, a 1-methylbutyl group, a 1-ethylpropyl group, a 2-methylbutyl group, an i-amyl group, a neopentyl group, a 1,2-dimethylpropyl group, a 1,1-dimethylpropyl group, a t-amyl group, a 1,3-dimethylbutyl group, a 3,3-dimethylbutyl group, a 2-ethylbutyl group, a 2-ethyl-2-methylpropyl group, a 1-methylheptyl group, a 2-ethylhexyl group, a 1,5-dimethylhexyl group, a t-octyl group, a branched nonyl group, a cyclopropyl group, a cyclopropylmethyl group, a cyclobutyl group, a cyclobutylmethyl group, a cyclopentyl group, a cyclohexyl group, a cyclohexylmethyl group, a cycloheptyl group, a cyclooctyl group, a cyclohexylpropyl group, a norbornyl group (C7), an adamantyl group (C10), and a cyclopentylethyl group.

In the invention, the alkenyl group represented by $R^6$ may or may not have a substituent group. Examples of the alkenyl group include an alkenyl group having 1 to 10 carbon atoms, and an alkenyl group having 1 to 8 carbon atoms is more preferable.

The alkenyl group having 1 to 10 carbon atoms can be any of a linear, a branched, or a cyclic alkenyl group, and preferred examples thereof include a vinyl group, an isopropenyl group, a 2-propenyl group, a 2-methyl-propenyl group, a 1-methyl-1-propenyl group, a 1-butenyl group, a 3-butenyl group, a 1-methyl-1-butenyl group, a 1,1-dimethyl-3-butenyl group, a 1-pentenyl group, a 2-pentenyl group, a 1-ethyl-1-pentenyl group, a 1-hexenyl group, a 1-heptenyl group, a 2,6-dimethyl-5-heptenyl group, a 1-cyclopentenyl group, a 2-cyclopentenylmethyl group, a cyclohexenyl group, a 1-methyl-2-cyclohexenyl group, and an octenyl group.

In the invention, the aryl group represented by $R^6$ may or may not have a substituent group. Examples of the aryl group include an aryl group having 6 to 10 carbon atoms, and an aryl group having 6 to 8 carbon atoms is more preferable.

Preferred examples of the aryl group having 6 to 10 carbon atoms include a phenyl group and a naphthyl group.

In the invention, the aralkyl group represented by $R^6$ may or may not have a substituent group. Examples of the aralkyl group include an aralkyl group having 7 to 10 carbon atoms.

Preferred examples of the aralkyl group having 7 to 10 carbon atoms represented by $R^6$ include a benzyl group, a 1-phenylethyl group, a 2-phenylethyl group, a 3-phenylpropyl group, a 4-phenylbutyl group, a styryl group (Ph-CH=CH— group), a cinnamyl group (Ph-CH=CHCH$_2$— group), a 1-benzocyclobutenyl group, and a 1,2,3,4-tetrahydronaphthyl group.

When the group represented by $R^6$ has a substituent group, it may be additionally substituted with a carboxy group and/or a sulfo group, and it also may contain a substituent group other than a carboxy group or a sulfo group. Examples of the substituent group include a carboxy group; a sulfo group; a halogen atom; a hydroxyl group; a nitro group; an amino group; an alkyl group, an alkoxy group, an alkoxycarbonyl group, an acyl group (—OCOR), and a hydroxyalkyloxy group (—O—R—OH) having 1 to 3 carbon atoms; and an aryl group and an aryloxy group having 6 to 10 carbon atoms. Further, in the aforementioned substituent groups, the expression "1 to 3 carbon atoms" indicates the number of carbons in the portion represented by R.

Specific examples of the above substituent group include, as a halogen atom, a fluoro group, a chloro group, a bromo group, and an iodo group. Examples of an alkyl group, an alkoxy group, an alkoxycarbonyl group, an acyl group, and a hydroxyalkyloxy group (—O— $(CH_2)_n$—OH) having 1 to 3 carbon atoms include a methyl group, an ethyl group, a n-propyl group, an i-propyl group, a methoxy group, an ethoxy group, a n-propoxy group, a methoxycarbonyl group, an ethoxycarbonyl, ethanoyl group, a propanoyl group, a butanoyl group, a hydroxyethyloxy group, and a hydroxypropyloxy group.

Of these, preferred examples of the above substituent group include a carboxy group, a sulfo group, a halogen atom such as a fluoro group, a chloro group, and a bromo group, a hydroxy group, a nitro group, an amino group, a methyl group, an ethyl group, a n-propyl group, an i-propyl group, a methoxy group, an ethoxy group, a n-propoxy group, a methoxycarbonyl group, an ethoxycarbonyl, ethanoyl group, a propanoyl group, and a butanoyl. More preferably, it is a carboxy group, a sulfo group, a halogen atom such as a fluoro group and a chloro group, a hydroxy group, a methyl group, an ethyl group, a methoxy group, an ethoxy group, a methoxycarbonyl group, an ethoxycarbonyl, ethanoyl group, a propanoyl group, or a butanoyl group. Still more preferably, it is a carboxy group, a sulfo group, a hydroxy group, a methoxy group, an ethoxy group, a methoxycarbonyl group, an ethoxycarbonyl, or an ethanoyl group. Further, as having higher neutralization efficiency by an organic acid, the carboxy group, sulfo group, or hydroxy group is particularly preferable.

Further, the aforementioned substituent group may be substituted with more than one time with the same substituent group.

Preferred embodiment of the organic acid of the invention is represented by the following formula (3C).

[Chemical formula 5]

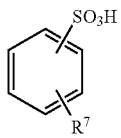
(3C)

In the formula (3C), $R^7$ represents a carboxy group; a sulfo group; a halogen atom; a hydroxy group; a nitro group; an amino group; an alkyl group, an alkoxy group, an alkoxycarbonyl group, an acyl group (—OCOR), a hydroxyalkyloxy group (—O—R—OH) having 1 to 3 carbon atoms; and an aryl group and an aryloxy group having 6 to 10 carbon atoms. Further, in the aforementioned substituent groups, the expression "1 to 3 carbon atoms" indicates the number of carbon atoms in the portion represented by R.

$R^7$ may be substituted at any position on benzene ring. However, relative to the sulfo group, the para position and ortho position are preferable, and the para position is more preferable.

Of those described above, $R^7$ is preferably a carboxy group, a sulfo group, a hydroxy group, or an alkyl group having 1 to 3 carbon atoms.

Examples of the organic acid used in the invention include the followings.

[Chemical formula 6]

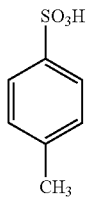

Examples of the organic acid having at least one carboxy group that may be used in the invention include acetic acid, phenylacetic acid, phenoxyacetic acid, chloroacetic acid, ethyl dimethylacetic acid (2,2-dimethylbutanoic acid), propionic acid (propanoic acid), 2-bromopropanoic acid, 3-phenylpropanoic acid, lactic acid, butyric acid (butanoic acid), isobutyric acid, 2-methylbutanoic acid, pentanoic acid, caproic acid (hexanoic acid), caprylic acid (octanoic acid), capric acid (decanoic acid), cyclohexane carboxylic acid, gluconic acid ((2R,3S,4R,5R)-2,3,4,5,6-pentahydroxyhexanoic acid), acrylic acid (2-propenoic acid), methacrylic acid (2-methylprop-2-enoic acid), citric acid, malonic acid (propanedioic acid), succinic acid (butanedioic acid), 2,3-dihydroxybutanedioic acid (tartaric acid), adipic acid (hexanedioic acid), 2-bromopentanedioic acid, 3,3-dimethylpentanedioic acid, 2,4-dichloropentanedioic acid, glycine, benzoic acid, o-toluic acid (o-methylbenzoic acid), m-toluic acid, p-chlorobenzoic acid, o-bromobenzoic acid, p-nitrobenzoic acid, phthalic acid, terephthalic acid, salicylic acid (2-hydroxybenzoic acid), acetyl salicylic acid (2-acetoxybenzoic acid), anthranilic acid (o-$H_2C_6H_4COOH$), m-aminobenzoic acid, p-methoxybenzoic acid (anisic acid), p-sec-butylbenzoic acid, and 2,4,6-trimethylbenzoic acid (mesitoic acid).

Examples of the organic acid having at least one sulfo group that may be used in the invention include methane sulfonic acid, aminomethane sulfonic acid, ethane sulfonic acid, 2-aminoethane-1-sulfonic acid, cyclohexylaminoethane sulfonic acid, benzene sulfonic acid, p-chlorobenzene sulfonic acid, p-toluene sulfonic acid, o-phenol sulfonic acid, p-phenol sulfonic acid, p-aminobenzene sulfonic acid, 4-nitrobenzene sulfonic acid, 3-amino-4-methoxybenzene sulfonic acid, 2,4-diaminobenzene sulfonic acid, trifluoromethane sulfonic acid, pentafluoroethane sulfonic acid, and heptafluoropropane sulfonic acid.

Of these, preferred examples thereof include non-polymerizable acetic acid, phenylacetic acid, phenoxyacetic acid, chloroacetic acid, propionic acid (propanoic acid), 2-bromopropanoic acid, 3-phenylpropanoic acid, lactic acid, butyric acid (butanoic acid), benzoic acid, phthalic acid, terephthalic acid, salicylic acid (2-hydroxybenzoic acid), acetylsalicylic acid (2-acetoxybenzoic acid), citric acid, gluconic acid, methane sulfonic acid, ethane sulfonic acid, benzene sulfonic acid, p-chlorobenzene sulfonic acid, p-toluene sulfonic acid, p-phenol sulfonic acid, and 4-nitrobenzene sulfonic acid. More preferably, it is acetic acid, phenylacetic acid, chloroacetic acid, propionic acid (propanoic acid), lactic acid, butyric acid (butanoic acid), citric acid, gluconic acid, methane sulfonic acid, ethane sulfonic acid, benzene sulfonic acid, p-chlorobenzene sulfonic acid, p-toluene sulfonic acid, or p-phenol sulfonic acid, and still more preferably it is non-polymerizable acetic acid, phenylacetic acid, chloroacetic acid, lactic acid, citric acid, gluconic acid, methane sulfonic acid, ethane sulfonic acid, benzene sulfonic acid, p-chlorobenzene sulfonic acid, p-toluene sulfonic acid, or p-phenol sulfonic acid. Further, as p-toluene sulfonic acid is useful for pH adjustment in broad range, it is particularly preferable. The organic acid may be used either singly or in combination of two or more.

According to the preferred embodiment, the monomer composition of the invention contains the organic acid in an amount of 0.0001 to 5 parts by weight relative to 100 parts by weight of the unsaturated polyalkylene glycol ether-based monomer. Preferably, it is 0.0005 to 4 parts by weight, more preferably 0.001 to 3 parts by weight, still more preferably 0.005 to 2.5 parts by weight, and particularly preferably 0.01 to 2 parts by weight. When the organic acid is contained in the range of 0.0001 to 5 parts by weight, desired pH adjustment can be made, and therefore it is desirable. Further, the expression "100 parts by weight of the unsaturated polyalkylene glycol ether-based monomer" means the weight of an unsaturated polyalkylene glycol ether-based monomer which is obtained on the assumption that unsaturated alcohol and alkylene oxide as raw materials have completely reacted (see, the production method described below). Further, the amount of organic acid described above means the addition amount of the aforementioned acetic acid, lactic acid, p-toluene sulfonic acid, or the like that is used for a neutralization step. Further, when two or more types of organic acids are used in combination, it represents their total amount.

The organic acid contained in the monomer composition of the invention is used, regarding the method for producing an unsaturated polyalkylene glycol ether-based monomer described below (i.e., alkylene oxide is added to unsaturated alcohol), for neutralization of an alkali system after the production, and it is present as it is in the composition. Since the monomer composition of the invention is an aqueous solution, the organic acid which may be contained in the monomer composition may be present in a dissociated state (for example, acetic acid is present as $CH_3COO^-$ and $H^+$ in the composition). Thus, when an organic acid is present as ion form as a result of dissociation, the content of the organic acid present in the monomer composition is calculated based on content of anions of the organic acid which are contained in the monomer composition ($CH_3COO^-$ for acetic acid, for example).

The content of organic acid in the monomer composition of the invention can be identified and quantified by using NMR measurement, acid titration, ion chromatography, or the like in combination. When the content of organic acid is obtained by $^1H$-NMR measurement, the measurement can be made by comparing integrated values of the peaks derived from an organic acid with those of the peaks derived from other components, in the same manner as the measurement of content of an unsaturated polyalkylene glycol ether-based monomer described above. Further, even when a monomer composition contains a volatile component, the measurement can be made in the same manner as the measurement of content of an unsaturated polyalkylene glycol ether-based monomer described above.

Meanwhile, a commercially available reagent can be used as an organic acid. Further, when the reagent is in diluted form like an aqueous solution, it may be contained in the monomer composition such that the net amount of the organic acid is in the content range described above. Further, when the organic acid is in solid form, it may be used after dilution with water or a solvent within the range that the stability of the monomer composition of the invention is not affected by it.

3. Water

The monomer composition of the invention contains water.

According to the preferred embodiment, the monomer composition of the invention contains water in an amount of 1 to 50 parts by weight relative to 100 parts by weight of the unsaturated polyalkylene glycol ether-based monomer. Preferably, it is 3 to 45 parts by weight, more preferably 5 to 40 parts by weight, still more preferably 7 to 35 parts by weight, and particularly preferably 10 to 30 parts by weight. When water is contained in the range of 1 to 50 parts by weight, a softening point allowing easy handlability can be achieved, and therefore it is desirable.

Content of water in the composition of the invention can be quantified by measuring moisture with Karl Fischer Moisture meter.

4. Others

The monomer composition of the invention may contain, in addition to the components described above, a catalyst and a solvent which may be used for production of an unsaturated polyalkylene glycol ether-based monomer, impurities mixedly present in raw materials, by-products generated by the reaction or the like.

(1) Catalyst

As for the catalyst which may be contained in the monomer composition of the invention, an alkali catalyst suitable for the method for producing an unsaturated polyalkylene glycol ether-based monomer as described below (i.e., alkylene oxide is added to unsaturated alcohol) is preferable.

Examples of the alkali catalyst include alkali metals such as lithium, sodium, or potassium; alkali metal hydrides such as lithium hydride, sodium hydride, or potassium hydride; organic lithium compounds such as n-butyl lithium; sodium amide; and metal hydroxides such as lithium hydroxide, sodium hydroxide, or potassium hydroxide. Any of these alkali catalysts may be used alone, or two or more of these may be used in combination. Of these, in terms of the handlability and economic efficiency, sodium hydride, sodium hydroxide, potassium hydroxide, sodium ethoxide, and sodium butoxide are preferable. Sodium hydride, sodium hydroxide, and potassium hydroxide are more preferable. Further, sodium hydroxide and potassium hydroxide are particularly preferable as they do not generate a compound with a low boiling point.

The amount of the alkali catalyst which may be contained in the monomer composition of the invention is generally 0.001 to 5% by weight, preferably 0.005 to 3% by weight, more preferably 0.01 to 2% by weight, still more preferably 0.025° to 1.5% by weight, and particularly preferably 0.05 to 1% by weight. The alkali catalyst contained within the range of 0.001 to 5% by weight is preferred for progress of the addition reaction described below, and therefore it is desirable.

Since the monomer composition of the invention is an aqueous solution, the alkali catalyst which may be contained in the monomer composition is present in dissociated form (sodium hydroxide is present as $Na^+$ and $OH^-$ in the composition, for example). Thus, when an alkali catalyst is dissociated and present as an alkali metal ion and its counter ion, the amount of alkali metal ion in the monomer composition is 5 to 30,000 ppm by weight, preferably 25 to 20,000 ppm by weight, more preferably 50 to 12,500 ppm by weight, still more preferably 100 to 10,000 ppm by weight, particularly preferably 150 to 7,500 ppm by weight, and most preferably 200 to 7,000 ppm by weight. Further, the amount of the alkali catalyst which may be contained in the monomer composition is related to the amount of an alkali catalyst used for the addition reaction.

According to the preferred embodiment, the alkali metal ion is, relative to 100 parts by weight of the unsaturated polyalkylene glycol ether-based monomer, 5 to 30,000 ppm by weight, preferably 25 to 20,000 ppm by weight, more preferably 50 to 12,500 ppm by weight, still more preferably 100 to 10,000 ppm by weight, particularly preferably 150 to 7,500 ppm by weight, and most preferably 200 to 7,000 ppm by weight.

Content of the alkali metal ion in the composition of the invention can be identified and quantified by Inductively Coupled Plasma (ICP) Emission Spectrometry method. For example, the measurement can be made by using high-frequency Inductively Coupled Plasma-Atomic Emission Spectrometry (ICP-AES) like CIROS-120.

(2) Solvent

According to the invention, a solvent other than water can be also contained. However, it is preferable that only water be contained as a solvent. The solvent which may be contained is not specifically limited, if it does not have an effect on the stability of the monomer composition of the invention.

When a solvent other than water is contained, the content is preferably 1 to 8% by weight in the monomer composition.

(3) Other Components

According to the invention, impurities or stabilizing agents that are mixedly present in raw materials, by-products generated by the reaction, or a stabilizing agent used for storage stability of the monomer composition may be contained.

Examples of the impurities that are mixedly present in raw materials include unsaturated aldehyde included in alkenyl alcohol as a raw material for the unsaturated polyalkylene glycol ether-based monomer and a stabilizing agent contained in the organic acid. Although it is described below, there can be a case in which 3-methyl-3-buten-1-ol contains 3-methyl-2-butenal (3-methylcrotonaldehyde) as impurities, for example.

For obtaining the polymer with high purity, it is preferable that the content of polyalkylene glycol be controlled to 1 to 10% by weight, more preferably 1 to 8% by weight, and still more preferably 1 to 5% by weight in the monomer composition of the invention. Content of the polyalkylene glycol can be measured by GPC as described in the examples given below.

When the impurities, by-products, and/or stabilizing agent or the like are contained, their total content is preferably 1 to 8 parts by weight relative to 100 parts by weight of the monomer. When it is within the range, it has only a minor effect on polymerization.

Examples of the stabilizing agent which may be contained according to the invention include a polymerization inhibitor such as dithiocarbamic acid salts, manganese salts, hydroxylamine compounds, nitiroso compounds, and N-oxyl compounds.

When such polymerization inhibitor is contained, the total content is preferably 100 to 1000 ppm by weight relative to 100 parts by weight of the monomer. When it is within the range, it has only a minor effect on polymerization.

The monomer composition of the invention is obtained by the production method described below, and it contains the components described above and has pH adjusted to 4 to 13. pH of the monomer composition of the invention is preferably pH 5 to pH 13, more preferably pH 6 to pH 13, still more preferably pH 6 to pH 12, and particularly preferably pH 7 to pH 12. When pH is within the range of from pH 4 to pH 13, it is difficult for the monomer to decompose, and therefore it is desirable.

Although the reason for excellent stability of the monomer composition of the invention remains unclear, it is believed as follows. However, the invention is not limited to the following speculations at all. As a problem of a monomer composition caused by insufficient stability, there is a precipitation of an alkali catalyst used for production from a monomer composition, which yields a heterogeneous monomer composition. As a result, it is believed that turbidity, separation, precipitation or the like occurs. Meanwhile, the monomer composition of the invention contains an organic acid, and an organic acid is partially dissociated in the monomer composition. For such reasons, it is suspected that ions derived from an alkali catalyst (i.e., alkali metal ions), which is dissociated in the monomer composition, are stabilized by an interaction with ions derived from the dissociated organic acid (i.e., anions) to suppress the precipitation of the ions derived from an alkali catalyst (i.e., alkali metal ions).

Further, as the monomer composition of the invention contains an organic acid, the alkali property derived from an alkali catalyst present in the system can be neutralized. When the monomer composition is produced by using an alkali catalyst, pH is often higher than 13. However, since the monomer composition of the invention contains an organic acid, it has pH of from 4 to 13. Accordingly, there is an advantage that there is not much of a concern to have polyethylene glycol produced by decomposition of the monomer.

<Method for Producing Monomer Composition>

The method for producing the monomer composition containing unsaturated polyalkylene glycol ether-based monomer of the invention includes a reaction step for reacting alkenyl alcohol having 2 to 7 carbon atoms with alkylene oxide having 2 to 18 carbon atoms in the presence of an alkali metal to obtain an unsaturated polyalkylene glycol ether-based monomer, a neutralization step for neutralizing the reaction liquid obtained from the reaction step to pH 4 to pH 13 by using an organic acid, and a concentration adjustment step for adding water to the reaction liquid obtained from said reaction step to yield an aqueous solution. According to the invention, by adding polyalkylene glycol to unsaturated alcohol, the monomer composition containing unsaturated polyalkylene glycol ether-based monomer, which is a raw polymerization material for producing the polycarboxylic acid-based polymer, is obtained. The method for producing such monomer composition is also one aspect of the invention.

Herein below, the method for producing the monomer composition of the invention is explained.

(Reaction Step)

The method for producing the monomer composition of the invention includes a reaction step for reacting alkenyl alcohol having 2 to 7 carbon atoms with alkylene oxide having 2 to 18 carbon atoms in the presence of an alkali catalyst to obtain an unsaturated polyalkylene glycol ether-based monomer (herein below, the reaction is referred to as an "addition reaction"). With regard to the reaction step, the addition reaction can be carried out by a conventionally known method, and for example, the reaction can be carried out by mixing and stirring in the presence of an alkali catalyst under inter gas atmosphere such as nitrogen. Further, since alkylene oxide with small carbon number is present as gas at ordinary temperature and pressure, the addition reaction needs to be carried out under pressure by using a pressure-resistance vessel such as an autoclave.

The alkylene oxide used for the addition reaction is the origin of $(R^1O)_n$ in the chemical formula (1). Thus, as alkylene oxide, alkylene oxide having 2 to 18 carbon atoms can be used. Preferably, it is alkylene oxide having 2 to 8 carbon atoms, and more preferably 2 to 4 carbon atoms. Examples of the alkylene oxide having 2 to 18 carbon atoms include ethylene oxide, propylene oxide, 1,2-butylene oxide, 2,3-butylene oxide, and styrene oxide. Of these, ethylene oxide and propylene oxide are preferable. Ethylene oxide is more preferable. The alkylene oxide may be used either singly or in combination of two or more. When alkylene oxide is used in combination of two or more, it may be added in any form such as random addition, block addition, and alternate addition. When two or more types of alkylene oxides are used, it is preferable that ethylene oxide be used as an essential component. Further, terminal of an alkylene oxide added to unsaturated alcohol (i.e., $R^2$ in the chemical formula (1)) is a hydrogen atom or a hydrocarbon group having 1 to 30 carbon atoms. As the hydrocarbon group having 1 to 30 carbon atoms is explained in detail in the above, no further explanation is given.

The average addition mole number of alkylene oxide is 5 to 500. When the average addition mole number decreases, hydrophilicity of the unsaturated polyalkylene glycol ether-based monomer is deteriorated. On the other hand, when the average addition mole number increases, reactivity of the unsaturated polyalkylene glycol ether-based monomer is deteriorated. Thus, the average addition mole number of alkylene oxide is preferably 10 or more, more preferably 20 or more, still more preferably 40 or more, and even still more preferably 50 or more. Further, it is preferably 300 or less, more preferably 200 or less, still more preferably 150 or less, and even still more preferably 100 or less.

The alkenyl alcohol used for the addition reaction can be represented by YOH, and it is the origin of Y in the chemical formula (1) explained above. As alkenyl alcohol, alkenyl alcohol having 2 to 8 carbon atoms can be used. Preferred examples thereof include vinyl alcohol ($CH_2$=CH—OH), 1-methyl-vinyl alcohol ($CH_2$=C($CH_3$)—OH), 1-propen-1-ol ($CH_3$CH=CH—OH), 2-propen-1-ol (allyl alcohol) ($CH_2$=CH$CH_2$—OH), 2-methyl-2-propen-1-ol ($CH_2$=C($CH_3$)—$CH_2$—OH), 2-buten-1-ol ($CH_3$CH=CH$CH_2$—OH), 3-methyl-3-buten-1-ol ($CH_2$=C($CH_3$)—$CH_2$$CH_2$—OH), 3-methyl-2-buten-1-ol (prenol) ($CH_3$C($CH_3$)=CH$CH_2$—OH), 2-methyl-3-buten-1-ol ($CH_2$=CHCH($CH_3$)—$CH_2$—OH), 2-methyl-2-buten-1-ol ($CH_3$CH=C($CH_3$)—$CH_2$—OH), 1-methyl-2-buten-1-ol ($CH_3$CH=CHCH($CH_3$)—OH), 1-penten-1-ol ($CH_3$$CH_2$$CH_2$CH=CH—OH), 1-hexen-1-ol ($CH_3$$CH_2$$CH_2$$CH_2$CH=CH—OH), 5-hexene-1-ol ($CH_2$=CH$CH_2$$CH_2$$CH_2$$CH_2$—OH), 3-hepten-1-ol ($CH_3$$CH_2$$CH_2$CH=CH$CH_2$$CH_2$—OH), and 2-cyclohexen-1-ol. Of these, vinyl alcohol, 2-propen-1-ol (allyl alcohol), 2-methyl-2-propen-1-ol, 3-methyl-3-buten-1-ol, and 3-methyl-2-buten-1-ol (prenol) are preferable. 2-Methyl-2-propen-1-ol and 3-methyl-3-buten-1-ol are more preferable, and 3-methyl-3-buten-1-ol is still more preferable.

Further, alkenyl alcohol may contain unsaturated aldehyde as impurities. For example, 3-methyl-3-buten-1-ol may contain 3-methyl-2-butenal (3-methyl crotonaldehyde) as impurities. Since a great amount of unsaturated aldehyde may cause coloration, its content is preferably as small as possible. Acceptable amount for the unsaturated aldehyde contained in alkenyl alcohol is preferably about 0.5% by weight or less, more preferably 0.2% by weight or less, still more preferably 0.1% by weight or less, even still more preferably 0.07% by weight or less, and particularly preferably 0.05% by weight or less.

Examples of the inert gas used for the addition reaction includes helium, argon, and nitrogen or the like. The inert gas may be used either singly or in combination of two or more. From the viewpoint of easy obtainability and economic efficiency, nitrogen is particularly preferable among the inert gases.

Examples of the alkali catalyst used for the addition reaction include alkali metals such as lithium, sodium, or potassium; alkali metal hydrides such as lithium hydride, sodium hydride, or potassium hydride; organic lithium compounds such as n-butyl lithium; sodium amide; and metal hydroxides such as lithium hydroxide, sodium hydroxide, or potassium hydroxide. Any of these alkali catalysts may be used alone, or two or more of these may be used in combination. Of these, in terms of the handlability and economic efficiency, sodium hydride, sodium hydroxide, and potassium hydroxide are preferable. Sodium hydride, sodium hydroxide, and potassium hydroxide are more preferable.

The amount of the alkali catalyst used for the addition reaction is, relative to total amount of alkenyl alcohol and alkylene oxide, 0.001 to 10% by weight, preferably 0.005 to 6% by weight, more preferably 0.01 to 4% by weight, still more preferably 0.025 to 3% by weight, and particularly preferably 0.05 to 2% by weight.

The temperature for the addition reaction to produce the unsaturated polyalkylene glycol ether-based monomer is not specifically limited. However, since thermal decomposition progresses and amount of polyethylene glycol as by-product increases as the addition reaction temperature increases, it is necessary to control the temperature for the addition reaction to a suitable range so that only a pre-determined amount of impurities are contained in the reaction liquid. Thus, it is preferably in the range of 80 to 160° C. More preferably, it is in the range of 90 to 140° C., and still more preferably in the range of 90 to 120° C.

Further, pressure for the addition reaction is not specifically limited and can be suitably adjusted to have smooth progress of the addition reaction. However, it is not specifically limited, and is generally 1.0 MPa or less, preferably 0.9 MPa or less, and more preferably 0.8 MPa or less. Time for the addition reaction is not specifically limited and can be suitably adjusted to according to amount of charged unsaturated alcohol or addition amount of polyalkylene glycol. For example, it is within the range of 0.5 to 24 hours, and preferably 1 to 20 hours.

Average addition mole number of alkylene oxide added to unsaturated alcohol is determined based on the amount of charged unsaturated alcohol and addition amount of alkylene oxide. However, relative to the unsaturated alcohol, the desired amount of alkylene oxide can be added via one reaction or a plurality of reactions. For example, it is possible to add less than desired amount of alkylene oxide to unsaturated alcohol during the first reaction and rest amount of alkylene oxide is added to the obtained alkylene oxide adducts of unsaturated alcohol during the following reaction.

The method for producing the monomer composition of the invention includes a concentration adjustment step for adding water to the reaction liquid obtained from the reaction step to give an aqueous solution. The concentration adjustment step is not specifically limited it if is carried out after the reaction step, that is, it may be carried out before the neutralization step or after the neutralization step. When viscosity of the solution is low during the neutralization step, the neutralization progresses is quickly so that the concentration adjustment step is preferably carried out before the neutralization step.

According to the concentration adjustment step, water is added to the reaction liquid of unsaturated polyalkylene glycol ether-based monomer as obtained above to give an aqueous solution. As for the method of producing an aqueous solution, an unsaturated polyalkylene glycol ether-based monomer can be mixed with water, for example, and the unsaturated polyalkylene glycol ether-based monomer before being prepared into an aqueous solution may be a solid or a liquid in which the monomer is dissolved in a solvent other than water.

For the concentration adjustment step, water is preferably added in an amount of 1 to 50 parts by weight relative to 100 parts by weight of unsaturated polyalkylene glycol ether-based monomer. More preferably, it is 3 to 45 parts by weight, still more preferably 5 to 40 parts by weight, particularly preferably 7 to 35 parts by weight, and most preferably 10 to 30 parts by weight. When it is more than 50 parts by weight, the unsaturated polyalkylene glycol ether-based monomer composition stores and/or transports the monomers mostly consisting of water, and therefore it is economically unfavorable. When it is less than 1 part by weight, the unsaturated polyalkylene glycol ether-based monomer composition obtained in the invention may be present in a solid state, and in such case, the unsaturated-polyalkylene glycol ether-based monomer composition needs to be melted by heating at the time of use, which may lead to polymerization, hydrolysis, or thermal decomposition of unsaturated polyalkylene glycol ether-based monomer, or increase of POV. The water concentration is suitably set depending on types of a polyalkylene glycol-based monomer used, as described below.

For the concentration adjustment step, the temperature for concentration adjustment is not specifically limited. However, from the viewpoint of preventing boiling, it is preferably 30 to 95° C. It is more preferably 40 to 95° C., and still more preferably 50 to 95° C.

The method for producing the monomer composition of the invention includes a neutralization step for neutralizing the reaction liquid obtained from the reaction step to pH 4 to 13 by using an organic acid. Preferably, it is pH 5 to 13, more preferably pH 6 to 13, still more preferably pH 6 to 12, and particularly preferably pH 7 to 12. When the pH of the monomer composition after neutralization is higher than 13, catalyst salts may be precipitated. On the other hand, when pH is lower than 4, the monomers may decompose. Herein, the organic acid used for the neutralization step is not further described as the organic acid described above can be also used.

The temperature at the time of neutralization for the neutralization step is not specifically limited. However, from the viewpoint of productivity and monomer decomposition, it is preferably 30 to 80° C. It is more preferably 40 to 70° C., and still more preferably 40 to 60° C.

In the monomer composition which is obtained as described above, an unsaturated polyalkylene glycol ether-based monomer, an alkali catalyst, an organic acid, and water are contained. It is believed that the alkali catalyst is dissociated as ions in the composition. Further, the organic acid may be also in the dissociated form or undissociated form. Any one of those forms is included in the present invention.

The monomer composition as obtained above has no turbidity even after storage for a long period of time, regardless of the amount of catalyst, and therefore is stable. For such reasons, the monomer composition of the invention is desirably used as a raw material for the polymer described below, even after storage for a long period of time. As represented in the following examples, the monomer composition of the invention exhibits no change in appearance even after storage for 7 days at 50° C., or 10 days at 50° C., exhibiting stability.

<Use of Monomer Composition>

The monomer composition of the invention is desirably used as a raw material for producing the polycarboxylic acid-based polymer which is described below. In addition, it may be used as a photosensitive resin composition, that is, a photosensitive film and a photosensitive resist can be obtained by using the monomer composition.

When the monomer composition of the invention is used as a photosensitive resin composition, a monomer composition, a compound having an epoxy group, and a photopolymerization initiator, and if it is necessary, a photopolymerizable monomer and/or oligomer other than the monomer composition, and the above various additives are homogeneously contained in the photosensitive resin composition, for example. Further, to be used as resist ink for color filter, the photosensitive resin composition may contain a pigment. In the above photosensitive resin composition, content of each component can be suitably adjusted.

By coating the above photosensitive resin composition on a substrate and drying, a photosensitive layer is formed. Further, according to selective exposure with light radiation, the exposed region is cured while the unexposed region is dissolved and removed (developed) using an alkali solution or the like to form a desired pattern. As for the above coating method, a commonly used method such as solution immersion; spray method; and coating method using a roll coater, a slit coater, a bar coater, and spinner or the like can be adopted. The coating film is formed to have about 0.2 to 100 μm, preferably 1 to 10 μm film thickness after drying. Examples of light (radiation light) used for light radiation include visible light, ultraviolet light, electronic beam, X ray, α ray, β ray, and γ ray. The composition can be also cured by heating. From the viewpoint of economic performance and efficiency, ultraviolet light is preferable. For ultraviolet radiation, a low pressure mercury lamp, a high pressure mercury lamp, an ultra-high pressure mercury lamp, a metal halide lamp, an arc lamp, and a xenon lamp or the like are used.

By subjecting the photosensitive layer composed of the resin composition of the invention, which is formed on a substrate, to selective exposure using light, carrying out development with a development liquid, and removing a region not irradiated with radiation light, patterning of a coating film can be achieved. Examples of the development method include a liquid mounting method, a dipping method, and a swing immersion method.

Examples of the development liquid for patterning using the composition of the invention include, for example, an aqueous alkali solution, a water soluble organic solvent, a mixture thereof, and a mixture thereof further added with a surfactant agent. Preferably, an aqueous alkali solution or a mixture of an aqueous alkali solution and a surfactant agent is used.

To improve alkali resistance after alkali development, it is preferable to carry out epoxy curing by heating an obtained pattern. According to the heating treatment, durability against strong alkali water is improved, and also various properties required for a solder resist such as adhesion to glass and metals such as copper, heat resistance and surface hardness are improved. The heating treatment is carried out in the temperature range of preferably 80 to 250° C., and more preferably 120 to 220° C. for 1 to 30 min on a hot plate or 10 to 120 min in an oven.

The photosensitive resin composition as obtained above can be desirably used for a color filter or the like of a color liquid crystal display.

<Method for Producing Polycarboxylic Acid-Based Polymer>

The monomer composition of the invention is preferably used a raw material for producing the polycarboxylic acid-based polymer.

By reacting the monomer composition of the invention (that is, a composition containing unsaturated polyalkylene glycol ether-based monomer) as a raw material with the unsaturated acid-based compound (monomer) represented by the chemical formula (2) in the presence of a polymerization initiator, radical polymerization of an unsaturated double bond each contained in unsaturated polyalkylene glycol ether-based monomer and unsaturated acid-based monomer progresses to yield a copolymer thereof (that is, polycarboxylic acid-based polymer) (see Examples 5 to 8 given below). By using the copolymer as cement admixture, cement admixture with no performance fluctuation is obtained. Further, in the present specification, the polycarboxylic acid-based polymer of the invention may be also simply referred to as a "polymer."

Herein below, the method for producing a polymer by using the monomer composition of the invention is described.

The polymer of the invention is obtained by using the monomer composition of the invention described in detail in the above and by reacting the unsaturated polyalkylene glycol ether-based monomer contained in the monomer composition and the unsaturated acid-based monomer represented by the following chemical formula (2):

[Chemical formula 7]

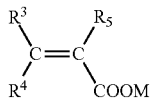

(2)

[in the formula, $R^3$, $R^4$, and $R^5$ each independently represent a hydrogen, a methyl group, or a —$(CH_2)_p$COOH group (in which p is an integer of from 0 to 2), and M is a hydrogen atom, a metal atom, an ammonium group, or an organic amine group].

Specifically, the method for producing the polycarboxylic acid-based polymer of the invention includes a reaction step for reacting alkenyl alcohol having 2 to 7 carbon atoms with alkylene oxide having 2 to 18 carbon atoms in the presence of an alkali catalyst to give an unsaturated polyalkylene glycol ether-based monomer, a concentration adjustment step for adding water to the reaction liquid obtained from the above reaction step to yield an aqueous solution, a neutralization step for neutralizing the above reaction liquid obtained from the reaction step to pH 4 to pH 13 by using an organic acid, and a polymerization step for obtaining the polycarboxylic acid-based polymer by using the monomer composition obtained after the above neutralization step and reacting the unsaturated polyalkylene glycol ether-based monomer contained in the monomer composition with the unsaturated acid-based monomer represented by the following chemical formula (2):

[Chemical formula 8]

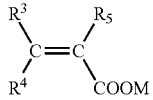

(2)

[in the formula, $R^3$, $R^4$, and $R^5$ each independently represent a hydrogen, a methyl group, or a —$(CH_2)_p$COOH group (in which p is an integer of from 0 to 2), and M is a hydrogen atom, a metal atom, an ammonium group, or an organic amine group].

Herein below, the method for producing polycarboxylic acid-based polymer of the invention is described. However, since the steps till the obtainment of the monomer composition (that is, the reaction step for obtaining unsaturated polyalkylene glycol ether-based monomer, concentration adjustment step, and neutralization step) have been already described regarding the method for producing the monomer composition, no further description is given therefor.

First, the polymerization step for reacting the unsaturated polyalkylene glycol ether-based monomer contained in the monomer composition and unsaturated acid-based monomer is described.

Examples of the unsaturated acid-based monomer represented by the chemical formula (2) include unsaturated monocarboxylic acid such as acrylic acid, methacrylic acid, and crotonic acid, unsaturated dicarboxylic acid such as maleic acid, maleic anhydride, fumaric acid, itaconic acid, and citraconic acid, and monovalent metals salts, divalent metal salts, ammonium salts, and organic amine salts thereof. It may be used either singly or in combination of two or more. Among those unsaturated acid-based monomers, from the viewpoint of polymerization property, acrylic acid, methacrylic acid, maleic acid, and monovalent salts thereof are preferable. Acrylic acid, maleic acid, and monovalent salts thereof are more preferable.

Use amount of the raw material (that is, monomer) is not specifically limited. However, according to a preferred embodiment, each of the unsaturated polyalkylene glycol ether-based monomer and the unsaturated acid-based monomer can be contained in an amount of 1% by weight or more relative to 100% by weight of the total amount of the two raw material compounds described above (that is, monomer). Further, content of the unsaturated polyalkylene glycol ether-based monomer is preferably 5% by weight or more, more preferably 10% by weight or more, still more preferably 20% by weight or more, and particularly preferably 40% by weight or more. By preparing it in such state, excellent dispersion performance can be obtained when an obtained copolymer is used as cement admixture. Further, from the viewpoint of having smooth polymerization reaction, the repeating unit derived from unsaturated polyalkylene glycol ether-based monomer corresponds to 50% by mole or less of the entire repeating units in the obtained copolymer. Further, from the viewpoint of enhancing the dispersion performance when used as cement admixture, it is preferable that the unsaturated acid-based monomer essentially contains (meth)acrylic acid (salts).

Further, in addition to the aforementioned two raw material compounds (that is, monomer), other monomer which is copolymerizable with them may be used for copolymerization of the polymerization step. Further, use amount of other monomer is, relative to 100% by weight of the total amount of raw material compounds (that is, monomer), preferably 0 to 70% by weight, more preferably 0 to 50% by weight, still more preferably 0 to 30% by weight, and particularly preferably 0 to 10% by weight. Other monomer is not specifically limited if it is a compound copolymerizable with the unsaturated polyalkylene glycol ether-based monomer and unsaturated acid-based monomer described above. One or two or more types of the following compounds can be used.

Half esters and diesters between unsaturated dicarboxylic acids such as maleic acid, maleic anhydride, fumaric acid, itaconic acid, and citraconic acid and alcohol having 1 to 30 carbon atoms; half amides and diamides between the unsaturated dicarboxylic acids and amine having 1 to 30 carbon atoms; half esters and diesters between alkyl (poly)alkylene glycol, in which 1 to 500 mole of alkylene oxide having 2 to 18 carbon atoms are added to the alcohol or amine, and the unsaturated dicarboxylic acids; half esters and diesters between glycol having 2 to 18 carbon atoms or polyalkylene glycol, in which 2 to 500 mole of alkylene oxide are added to the glycol, and the unsaturated dicarboxylic acid; esters between alcohol having 1 to 30 carbon atoms and unsaturated monocarboxylic acids such as methyl (meth)acrylate, ethyl (meth)acrylate, propyl (meth)acrylate, glycidyl (meth) acrylate, methylcrotonate, ethylcrotonate, and propylcrotonate; esters between alkoxy (poly)alkylene glycol, in which 1 to 500 mole of alkylene oxide having 2 to 18 carbon atoms are added to the alcohol having 1 to 30 carbons atoms, and the unsaturated monocarboxylic acids such as (meth)acrylic acid; addition products in which 1 to 500 mole of alkylene oxide having 2 to 18 carbon atoms are added to unsaturated monocarboxylic acids such as (poly)ethylene glycol monomethacrylate, (poly)propylene glycol monomethacrylate, and (poly)butylene glycol monomethacrylate; half amides between maleic amidic acid and glycol having 2 to 18 carbon atoms or polyalkylene glycol, in which 2 to 500 mole of alkylene oxide are added to the glycol.

(Poly)alkylene glycol di(meth)acrylates such as triethylene glycol di(meth)acrylate, (poly)ethylene glycol di(meth) acrylate, polypropylene glycol di(meth)acrylate, and (poly) ethylene glycol (poly)propylene glycol di(meth)acrylate; polyfunctional (meth)acrylates such as hexane diol di(meth) acrylate, trimethylolpropane tri(meth)acrylate, and trimethylolpropane di(meth)acrylate; (poly)alkylene glycol dimaleates such as triethylene glycol dimaleate and polyethylene glycol dimaleate; unsaturated sulfonic acids such as vinyl sulfonate, (meth)allyl sulfonate, 2-(meth)acryloxyethyl sulfonate, 3-(meth)acryloxypropyl sulfonate, 3-(meth) acryloxy-2-hydroxypropyl sulfonate, 3-(meth)acryloxy-2-hydroxypropyl sulfophenyl ether, 3-(meth)acryloxy-2-hydroxypropyloxysulfobenzoate, 4-(meth)acryloxybutyl sulfonate, (meth)acrylamide methyl sulfonic acid, (meth) acrylamide ethyl sulfonic acid, 2-methylpropane sulfonic acid(meth)acrylamide, and styrene sulfonic acid, and monovalent metal salts, divalent metal salts, ammonium salts, and organic amine salts thereof; amides between unsaturated monocarboxylic acids and amines having 1 to 30 carbon atoms, such as methyl (meth)acrylamide; vinyl aromatic compounds such as styrene, α-methylstyrene, vinyltoluene, and p-methylstyrene; alkane diol mono(meth)acrylates such as 1,4-butane diol mono(meth)acrylate, 1,5-pentane diol mono(meth)acrylate, and 1,6-hexane diol mono(meth)acrylate; and dienes such as butadiene, isoprene, 2-methyl-1,3-butadiene, and 2-chloro-1,3-butadiene.

Unsaturated amides such as (meth)acrylamide, (meth) acrylalkylamide, N-methylol (meth)acrylamide, and N,N-dimethyl (meth)acrylamide; unsaturated cyans such as (meth)acrylonitrile and α-chloro acrylonitrile; unsaturated esters such as vinyl acetate and vinyl propionate; unsaturated amines such as aminoethyl (meth)acrylate, methylaminoethyl (meth)acrylate, dimethylaminoethyl (meth)acrylate, dimethylaminopropyl (meth)acrylate, dibutylaminoethyl (meth)acrylate, and vinyl pyridine; divinyl aromatic compounds such as divinyl benzene; cyanurates such as triallyl cyanurate; allyls such as (meth)allyl alcohol and glycidyl (meth)allyl ether; vinyl ethers or allyl ethers such as methoxypolyethylene glycol monovinyl ether, polyethylene glycol monovinyl ether, methoxypolyethylene glycol mono(meth)allyl ether, and polyethylene glycol mono(meth)allyl ether; and siloxane derivatives such as polydimethylsiloxane propylaminomaleic amide acid, polydimethylsiloxane aminopropylene aminomaleic amide acid, polydimethylsiloxane-bis-(propylaminomaleic amide acid), polydimethylsiloxane-bis-(dipropylene aminomaleic amide acid), polydimethylsiloxane-(1-propyl-3-acrylate), polydimethylsiloxane-(1-propyl-3-methacrylate), polydimethylsiloxane-bis-(1-propyl-3-acrylate), and polydimethylsiloxane-bis-(1-propyl-3-methacrylate).

To perform the reaction of the polymerization step described above, the raw materials described above (unsaturated polyalkylene glycol ether-based monomer and unsaturated acid-based compound monomer), and if it is necessary, other monomer are copolymerized using a polymerization initiator. The copolymerization may be performed by using a known polymerization technology, such as solution polymerization, bulk polymerization, or the like. The solution polymerization may be performed with batchwise or continuous type. The solvent used for polymerization is not specifically limited, and examples thereof include water; alcohol such as methanol, ethanol, and isopropanol; aromatic or aliphatic hydrocarbons such as benzene, toluene, xylene, cyclohexane, and n-hexane; ester compounds such as ethyl acetate; ketone compounds such as acetone and methyl ethyl ketone; and cyclic ether compounds such as tetrahydrofuran and dioxane. From the viewpoint of solubility of raw material compounds and copolymer obtained, it is preferable to use at least one solvent selected from a group consisting of lower alcohols having 1 to 4 carbon atoms and water. Among them, it is preferable to use water as a solvent from the viewpoint that the desolvent step is not presented.

When an aqueous solution polymerization is performed for the polymerization step, as a radical polymerization initiator, a water soluble polymerization initiator such as persulfates such as ammonium persulfate, sodium persulfate, or potassium persulfate; hydrogen peroxide; and a water soluble azo-based initiator such as an azoamidine compound such as 2,2'-azobis-2-methylpropionic amidine hydrochloride, a cyclic azoamidine compound such as 2,2'-azobis-2-(2-imidazolin-2-yl)propane hydrochloride, and an azonitrile compound such as 2-carbamoyl azoisobutyronitrile can be used. In this regard, a promoting agent such as alkali metal sulfite such as sodium hydrogen sulfite, meta bisulfite, sodium hypophosphite, Fe (II) salt such as Mohr's salt, sodiumhydroxymethanesulfinatedihydrate, hydroxyamine hydrochloride, thiourea, L-ascorbic acid (salt), or erysorbic acid (salt) may be used in combination. Of these, combination of hydrogen peroxide and a promoter such as L-ascorbic acid (salt) is preferable. Each of the radical polymerization initiator or promoting agent may be used either singly or in combination of two or more. Further, the polymerization temperature for carrying out the aqueous solution polymerization is not specifically limited. For example, it is 25 to 99° C., preferably 35 to 95° C., more preferably 40 to 92° C., and still more preferably 45 to 90° C. As used herein, the expression "polymerization temperature" means the temperature of a reaction solution in the reaction system of the polymerization step.

When a solution polymerization in which lower alcohol, aromatic or aliphatic hydrocarbon, an ester compound, or a ketone compound is used as a solvent is performed, peroxides such as benzoyl peroxide, lauroyl peroxide, and sodium peroxide; hydroperoxides such as t-butyl hydroperoxide and cumene hydroperoxide; and azo compounds such as azobisisobutyronitrile are used as a radical polymerization initiator. A promoting agent such as an amine compound can be also used in combination. When a mixture solvent of water and lower alcohol is used, it may be appropriately selected from various radical polymerization initiators described above, and combination of a radical polymerization initiator and a promoting agent. Further, the polymerization temperature for performing the solution polymerization is not specifically limited. For example, it is 25 to 99° C., preferably 40 to 90° C., more preferably 45 to 85° C., and still more preferably 50 to 80° C.

Further, when bulk polymerization is carried out, peroxides such as benzoyl peroxide, lauroyl peroxide, and sodium peroxide; hydroperoxides such as t-butyl hydroperoxide and cumene hydroperoxide; and azo compounds such as azobisisobutyronitrile are used as a radical polymerization initiator. The polymerization is carried out at the temperature of 50 to 200° C.

The method for adding each raw material to a reactor is not specifically limited. It may be any one of a method in which entire amounts are added to the reactor all at once at initial stage, a method in which entire amounts are added to the reactor in portions or continuously, and a method in which part of them is added to the reactor at initial stage and the rest are added to the reactor in portions or continuously. Specifically, there is a method in which entire amount of the unsaturated acid-based monomer and unsaturated polyalkylene glycol ether-based monomer are added continuously to the reaction vessel, a method in which part of the unsaturated acid-based monomer is added to the reaction vessel at initial stage and rest of the unsaturated acid-based monomer and entire amount of the unsaturated polyalkylene glycol ether-based monomer are continuously added to the reaction vessel, and a method in which part of the unsaturated acid-based monomer and part of the unsaturated polyalkylene glycol ether-based monomer are added to the reaction vessel at initial stage and then the rest of unsaturated acid-based monomer and the rest of unsaturated polyalkylene glycol ether-based monomer are alternately added to the reaction vessel in several divided portions. Further, it is also possible that, according to continuous or stepwise change of addition speed of each monomer to a reaction vessel during the reaction, the addition weight ratio of each monomer per unit time is changed in continuous or stepwise manner so that a mixture of copolymers having different constitutional ratio of repeating units in the copolymer can be synthesized during the polymerization reaction. Further, the radical polymerization initiator may be added to a reaction vessel from the beginning or added dropwise to a reactor. It is also possible to combine such procedures depending on purpose.

For purpose of adjusting molecular weight of a copolymer to be obtained, a chain transfer agent may be also used. The chain transfer agent is not specifically limited, and examples thereof include a thiol-based chain transfer agent such as mercaptoethanol, thioglycerol, thioglycolic acid, 2-mercaptopropionic acid, 3-mercaptopropionic acid, thiomalic acid, octyl thioglycolate, octyl 3-mercaptopropionate, and 2-mercaptoethanesulfonic acid; secondary alcohols such as isopropanol; phosphorous acid, hypophosphorous acid, and salts thereof (sodium hypophosphorous acid and potassium hypophosphorous acid), and lower oxides of sulfurous acid, hydrogen sulfurous acid, dithionic acid, metabisulfurous acid, and salts thereof (sodium sulfite, potassium sulfite, sodium hydrogen sulfite, potassium hydrogen sulfite, sodium dithionite, potassium dithionite, sodium metabisulfite, and potassium metabisulfite) and so on. It may be used either singly or in combination of two or more. Further, for purpose of adjusting the molecular weight of a copolymer to be obtained, it is also effective to use a monomer having high chain transfer property such as (meth)allyl sulfonic acids (salts) as "other monomer".

Further, regarding the method for producing the polycarboxylic acid-based polymer of the invention, time interval between end of the neutralization step and beginning of the polymerization step is preferably 6 hours or more.

Further, the time interval between end of the neutralization step and beginning of the polymerization step is preferably 12 hours or more, more preferably 24 hours or more, still more preferably 60 hours or more, particularly preferably 120 hours or more, and most preferably 240 hours or more. Since the monomer composition of the invention has excellent stability, even when a considerable amount of time more than the above-described time interval is present between the neutralization step and polymerization step, it can be preferably used as a raw material for production of the polymerization step. Further, although not specifically limited, the upper limit of the time interval is 1 year or less from the viewpoint of stability of the monomer composition. More preferably, it is 6 months or less, and still more preferably 3 months or less.

Further, regarding the time interval between end of the neutralization step and beginning of the polymerization step, the temperature of the monomer composition is preferably 50 to 90° C., more preferably 50 to 85° C., still more preferably 50 to 80° C., and particularly preferably 50 to 75° C. from the viewpoint of stability, although it is not specifically limited thereto.

During the time interval between end of the neutralization step and beginning of the polymerization step, storage form for the monomer composition is not specifically limited. As used herein, the term "storage" means keeping or maintaining without performing an operation such as stirring. For example, when neutralization is performed under stirring, the stirring is stopped after confirming the neutralization, and is kept until the next polymerization step, the time period with no stirring is referred to as storage. The storage form during the time interval between end of the neutralization step and beginning of the polymerization step includes, for example, storage in a vessel or a reactor in which the neutralization is performed, or storage in other vessel or reactor after transportation following the neutralization step. The reactor or vessel may be open or closed to atmospheric air. However, it is preferably stored in a close system which is filled with inert gas such as nitrogen and argon. The storage vessel is not specifically limited, and a reactor, a container, a drum can, an aboveground tank, an underground tank or the like is used. Regarding the materials of a reactor or vessel for storage, those can maintain sealing state during storage and hardly undergo decomposition or deterioration at the temperature of −50 to 150° C. are preferable. Preferred examples thereof include stainless (SUS), aluminum, iron, and glass. Further, when the vessel is stirred by shaking or the like periodically (for example, once a day) during the storage period, it is included in the time interval between end of the neutralization step and beginning of the polymerization step of the invention.

The method for producing a polymer according to the invention also includes transportation of the monomer composition due to the aforementioned storage. The term "transportation" means, among the operations accompanying transport of materials, an operation of moving by using a vessel for transport such as a container, a drum can, a petroleum can, or a polytank, and it is also referred to as "shipping". Regarding the materials of vessel for transport, those can maintain sealing state during transport and hardly undergo decomposition or deterioration at the temperature of −50 to 150° C. are preferable. Preferred examples thereof include stainless (SUS), aluminum, iron, and glass. According to the invention, the vessel for transport can be used only for transporting the polyalkylene glycol ether-based monomer, and it may be also used for storing it by itself.

Because the monomer composition of the invention has excellent stability, for the method of producing the polymer, even the time interval between end of the neutralization step and beginning of the polymerization step is ten days or more, it is unlikely to have any change in performance. As such, even when a monomer composition obtained after undergoing aging step is used as a raw material, a polymer with little performance fluctuation can be obtained.

The weight average molecular weight of the polymer that is obtained by the polymerization step is not specifically limited. For example, it is preferably 3,000 to 1,000,000, more preferably 5,000 to 500,000, and still more preferably 10,000 to 100,000. When it is within the range, the reaction can be easily controlled and the polymerization product can be easily handled, and thus there is an advantage that performance as a dispersing agent can be fully exhibited.

The polycarboxylic acid-based polymer obtained by the production method of the invention is obtained as, in preferred form, an aqueous solution containing the polycarboxylic acid-based polymer. As such, the polycarboxylic acid-based polymer obtained by the production method of the invention may be sometimes referred to as "the polycarboxylic acid-based polymer (composition)".

The polycarboxylic acid-based polymer (composition) obtained by the production method of the invention contains an organic acid, relative to 100 parts by weight of the polymer, preferably in an amount of 0.0002 to 1.3 parts by weight, more preferably 0.0001 to 1.0 parts by weight, and still more preferably 0.0005 to 0.75 parts by weight. Further, the polycarboxylic acid-based polymer (composition) of the invention contains an alkali metal ion, relative to 100 parts by weight of the polymer, preferably 0.0001 to 0.6 parts by weight, more preferably 0.0002 to 0.5 parts by weight, and still more preferably 0.0004 to 0.25 parts by weight. As for the content of organic acid and alkali metal ion in the polymer (composition), the same measurement as the measurement method for the content of organic acid and alkali metal ion in the monomer composition described above can be also used.

<Use of Polycarboxylic Acid-Based Polymer>

The polymer produced by the production method of the invention may be preferably used as cement admixture.

The cement admixture of the invention contains, as an essential component, the polymer produced by the production method of the invention, and the polymer may be used as an aqueous solution itself as obtained by the production method as main components of the cement admixture, or the polymer may be dried and prepared as powder.

The cement admixture of the invention can be used for various hydraulic materials, that is, cement composition such as cement and gypsum or other hydraulic materials. Specific examples of a hydraulic composition which contains hydraulic materials, water, and the cement admixture of the invention, and if necessary, fine aggregate (sand or the like) or coarse aggregate (crushed stones or the like) include cement paste, mortar, concrete, and plaster.

Among the hydraulic compositions described above, a cement composition using cement as a hydraulic materials is most common, and the cement composition contains the cement admixture of the invention, cement, and water as essential components. The cement composition corresponds to one preferred embodiment of the invention.

The cement used for the cement composition is not especially limited. Examples of the cement include: Portland cements (ordinary, high early strength, ultra high early strength, moderate heat, sulfate resistance, and low alkaline type thereof); various mixed cements (blast furnace cement, silica cement, fly ash cement); white Portland cement; alumina cement; ultra rapid hardening cement (one-clinker ultra rapid hardening cement, two-clinker ultra rapid hardening cement, and magnesium phosphate cement); grouting cements; oil well cements; low heat cements (low heat blast furnace cement, fly ash-mixed low heat blast furnace cement, belite-highly containing cement); ultra high strength cements; cement solidification materials; and ecocements (cements manufactured using one or more kinds of municipal refuse incinerated ash and sludge incinerated ash as a raw material). Further, fine powders such as blast furnace slag, fly ash, cinder ash, clinker ash, husk ash, silica fume, silica powder, and limestone powder, or plaster may be added. As the aggregate, in addition to gravel, crushed stone, water granulated slag, recycled aggregate, and the like, refractory aggregates such as silica aggregate, argillaceous aggregate, zircon aggregate, high alumina aggregate, silicon carbide aggregate, graphite aggregate, chromium aggregate, chrome-magnesite aggregate, and magnesia aggregate may be used.

In the cement composition, an unit quantity of water per cubic meter of the cement composition, a cement use amount, and a water/cement ratio are not particularly limited, and the unit quantity of water is preferably 100 kg/m$^3$ to 185 kg/m$^3$. The use amount of cement is preferably 250 kg/m$^3$ to 800 kg/m$^3$. The water/cement ratio (weight ratio) is preferably 0.1 to 0.7. It is preferable that the unit quantity of water is 120 kg/m$^3$ to 175 kg/m$^3$, the use amount of cement is preferably 270 kg/m$^3$ to 800 kg/m$^3$, and the water/cement ratio (weight ratio) is preferably 0.2 to 0.65. The cement admixture of the invention can be widely used at lean-mix design to rich-mix design. Thus, the cement admixture of the invention is effective for any of high strength concrete having a large unit quantity of cement and a small water/cement ratio, an ultra strength concrete which is in a range where the water/cement ratio (weight ratio) is small, that is, 0.3 or less, and lean-mix concrete having an unit quantity of cement of 300 kg/m$^3$ or less. As for the proportion of the cement admixture of the invention in the above-mentioned cement composition, although not specifically limited, the proportion of the polymer added is 0.01 to 5.0% by weight, preferably 0.02 to 2.0% by weight, and more preferably 0.05 to 1.0% by weight on the solid content basis relative to the weight of cement in a case where the cement admixture is used in mortar or concrete each including a hydraulic cement. According to the addition, various preferable effects such as a reduction in unit quantity of water, an increase in strength, and an improvement in durability are exhibited. If the above proportion is less than 0.01%, the performances might be insufficient. If it is used in a large amount like more than 5.0%, the effect is no more improved substantially, and therefore becomes economically disadvantageous.

The cement composition of the invention may contain a cement dispersing agent described below: lignin sulfonic acid salts; polyol derivatives; naphthalene sulfonic acid formalin condensates; melamine sulfonic acid formalin condensates; polystyrene sulfonic acid salts; amino sulfonic acids such as aminoaryl sulfonic acid-phenol-formaldehyde condensates as described in JP H01-113419 A; cement dispersing agents containing as component (a) a copolymer of a polyalkylene glycol mono(meth)acrylate ester-based compound and a (meth)acrylic acid-based compound and/or salt thereof, as a component (b) a copolymer of a polyalkylene glycol mono(meth)allyl ether-based compound and maleic anhydride and/or hydrolysate thereof and/or salt thereof, and as a component (c) a copolymer of a polyalkylene glycol mono(meth)allyl ether-based compound and polyalkylene glycol maleate ester, and/or salt thereof as described in JP H07-267705 A; concrete admixtures containing as a component A, a copolymer of polyalkylene glycol ester of (meth)acrylate and (meth)acrylic acid (salt), as a component B, a specific polyethylene glycol polypropylene glycol-based compound and as a component C, a specific surfactant agent as described in Japanese Patent No. 2508113;

A copolymer composed of polyethylene(propylene)glycol ester of (meth)acrylate, (meth)allyl sulfonic acid (salt), and (meth)acrylic acid (salt) as described in JP H01-226757 A; a copolymer composed of polyethylene(propylene)glycol ester of (meth)acrylate, (meth)allyl sulfonic acid (salt) or p-(meth)allyloxybenzene sulfonic acid (salt) and (meth) acrylic acid (salt) as described in JP H05-36377 B; a copolymer containing polyethylene glycol mono(meth)allyl ether and maleic acid (salt) as described in JP H04-149056 A; a copolymer composed of polyethylene glycol ester of (meth)acrylate, (meth)allyl sulfonic acid (salt), (meth) acrylic acid (salt), alkanediol mono(meth)acrylate, polyalkylene glycol mono(meth)acrylate, and an α,β-unsaturated monomer having an amide group in the molecule as described in JP H05-170501 A; a copolymer composed of alkoxypolyethylene glycol monoally ether and maleic anhydride or hydrolysates thereof, or salt thereof as described in JP H05-43288 A; a copolymer composed of polyethylene glycol monoallyl ether, maleic acid, and a monomer copolymerizable with these monomers, or salt thereof or ester thereof as described in JP S58-38380 B.

a copolymer composed of polyalkylene glycol mono (meth)acrylate ester-based monomer, (meth)acrylic acid-based monomer, and a monomer copolymerizable with these monomers as described in JP S59-18338 B; a copolymer composed of (meth)acrylate ester having sulfonic acid group and optionally a monomer copolymerizable with this monomers, or salt thereof as described in JP S62-119147 A; an esterified product between a copolymer composed of alkoxypolyalkylene glycol monoallyl ether and maleic anhydride, and a polyoxyalkylene derivative having an alkenyl group at the terminal as described in JP H06-271347 A; and an esterified product between a copolymer composed of alkoxypolyalkylene glycol monoallyl ether and maleic anhydride, and a polyoxyalkylene derivative having a hydroxyl group at the terminal as described in JP H06-298555 A. These cement dispersing agents may be used either singly or in combination of two or more types.

When the cement dispersing agent is used, the ratio between the polymer of the invention as a cement admixture and the cement dispersing agent is, in terms of weight ratio based on solid content basis (% by weight), preferably 1/99 to 99/1, more preferably 5/95 to 95/5, and still more preferably 10/90 to 90/10, although the optimum ratio varies depending on performance balance between the polymer and the cement dispersing agent.

Further, the cement composition may further contain other known cement additives (materials) that are exemplified below as (1) to (20).
(1) Water-soluble polymeric substances: unsaturated carboxylic acid polymers such as polyacrylic acid (sodium salt), polymethacrylic acid (sodium salt), polymaleic acid (sodium salt), and acrylic acid-maleic acid copolymer sodium salt; nonionic cellulose ethers such as methyl cellulose, ethyl cellulose, hydroxymethyl cellulose, hydroxyethyl cellulose, carboxymethyl cellulose, carboxyethyl cellulose and hydroxypropyl cellulose; polysaccharide derivative derived from alkylated or hydroxyalkylated derivative of polysaccharide, such as methyl cellulose, ethyl cellulose, hydroxyethyl cellulose and hydroxypropyl cellulose, by substitution of a part or all of hydroxyl hydrogen atoms with a hydrophobic substituent comprising a hydrocarbon chain containing 8 to 40 carbon atoms as a partial structure and an ionic hydrophilic substituent containing a sulfonic acid group or a salt thereof as a partial structure; polysaccharides produced by microbial fermentation such as yeast glucans, xanthan gum, β-1,3-glucans (linear or branched, e.g., curdlan, paramylon, pachyman, scleroglucan, laminaran) and the like; polyacrylamide; polyvinyl alcohol; starch; starch phosphoric acid ester; sodium alginate; gelatin; acrylic acid copolymers having an amino group in the molecule and quaternary products thereof.
(2) Polymer emulsions: copolymers of various vinyl monomer such as alkyl (meth)acrylates.
(3) Retarder selected from a group consisting of oxycarboxylic acid, its salt, sugars, and sugar alcohol: magnesium silicofluoride; phosphoric acid and salts thereof, or borate esters; aminocarboxylic acids and salts thereof; alkali-soluble proteins; humic acid; tannic acid; phenols; polyalcohols such as glycerol; phosphonic acids and derivatives thereof, such as aminotri(methylenephosphonic acid), 1-hydroxyethylidene-1,1-diphosphonic acid, ethylenediamine tetra(methylenephosphonic acid), diethylenetriamine penta (methylenephosphonic acid), and alkali metal salts or alkaline earth metal salts thereof, or the like.
(4) Early strengthening agents/accelerators: soluble calcium salts such as calcium chloride, calcium nitrite, calcium nitrate, calcium bromide and calcium iodide; chlorides such as iron chloride and magnesium chloride; sulfate salts; potassium hydroxide; sodium hydroxide; carbonate salts; thiosulfate salts; formic acid and formate salts such as calcium formate; alkanolamines; alumina cement; calcium aluminosilicate, or the like.
(5) Mineral oil-based antifoaming agents: kerosene, liquid paraffin, or the like.
(6) Fat and oil-based antifoaming agents: animal or vegetable oils, sesame oil, castor oil, and the alkylene oxide adducts thereof, or the like.
(7) Fatty acid-based antifoaming agents: oleic acid, stearic acid, and the alkylene oxide adducts thereof, or the like.
(8) Fatty acid ester-based antifoaming agents: glycerol monoricinolate, alkenylsuccinic acid derivatives, sorbitol monolaurate, sorbitol trioleate, natural waxes, or the like.
(9) Oxyalkylene type antifoaming agents: polyoxyalkylenes such as (poly)oxyethylene(poly)oxypropylene adducts; (poly)oxyalkyl ethers such as diethylene glycol heptyl ether, polyoxyethylene oleyl ether, polyoxypropylene butyl ether, polyoxyethylene polyoxypropylene 2-ethylhexyl ether, or oxyethylene oxypropylene adducts of higher alcohol having 12 to 14 carbon atoms; (poly)oxyalkylene(alkyl)aryl ethers such as polyoxypropylene phenyl ether or polyoxyethylene nonylphenyl ether; acetylene ethers produced by addition polymerization of an alkylene oxide onto an acetylene alcohol such as 2,4,7,9-tetramethyl-5-decyne-4,7-diol, 2,5-dimethyl-3-hexyne-2,5-diol or 3-methyl-1-butyn-3-ol; (poly)oxyalkylene fatty acid esters such as diethylene glycol oleate, diethylene glycol laurate or ethylene glycol distearate; (poly)oxyalkylene sorbitan fatty acid esters such as polyoxyethylene sorbitan monolaurate or polyoxyethylene sorbitan trioleate; (poly)oxyalkylene alkyl(aryl)ether sulfate ester salts such as polyoxypropylene methyl ether sulfate sodium salt or polyoxyethylene dodecylphenyl ether sulfate sodium salt; (poly)oxyalkylene alkylphosphate esters such as (poly)oxyethylene stearylphosphate; (poly)oxyalkylene alkylamines such as polyoxyethylene laurylamine; polyoxyalkyleneamides, or the like.
(10) Alcohol-based antifoaming agents: octyl alcohol, hexadecyl alcohol, acetylene alcohols, glycols, or the like.
(11) Amide-based antifoaming agents: acrylate polyamines, or the like.

(12) Phosphate ester-based antifoaming agents: tributyl phosphate, sodium octylphosphate, or the like.
(13) Metal soap-based antifoaming agents: aluminum stearate, calcium oleate, or the like.
(14) Silicone-based antifoaming agents: dimethylsilicone oil, silicone paste, silicone emulsions, organic group-modified polysiloxanes (polyorganosiloxanes such as dimethylpolysiloxane), fluorosilicone oils, or the like.
(15) Air-entraining (AE) agents: resin soaps, saturated or unsaturated fatty acids, sodium hydroxystearate, lauryl sulfate, ABSs (alkylbenzene sulfonates), LASs (linear alkylbenzene sulfonates), alkane sulfonates, polyoxyethylene alkyl(phenyl)ethers, polyoxyethylene alkyl(phenyl)ether sulfate esters or salts thereof, polyoxyethylene alkyl (phenyl)) ether phosphate esters or salts thereof, proteinic materials, alkenyl sulfosuccinates, α-olefin sulfonates, or the like.
(16) Other surfactant agents: polyalkylene oxide derivatives derived from aliphatic monohydric alcohols of 6 to 30 carbon atoms within the molecule, such as octadecyl alcohol or stearyl alcohol, alicyclic monohydric alcohols of 6 to 30 carbon atoms within the molecule, such as abietyl alcohol, monofunctional mercaptans of 6 to 30 carbon atoms within the molecule, such as dodecylmercaptan, alkylphenols of 6 to 30 carbon atoms within the molecule, such as nonylphenol, amines of 6 to 30 carbon atoms within the molecule, such as dodecylamine, or carboxylic acids of 6 to 30 carbon atoms within the molecule, such as lauric acid or stearic acid, by addition of not less than 10 moles of an alkylene oxide (s) such as ethylene oxide and propylene oxide; alkyldiphenyl ether sulfonic acid salts in which two sulfo-containing phenyl groups, which may optionally have an alkyl group or alkoxy group as a substituent group, is bonded via ether bonding; various anionic surfactant agents; various cationic surfactant agents such as alkylamine acetates and alkyltrimethyl ammonium chlorides; various nonionic surfactant agents; various amphoteric surfactant agents, or the like.
(17) Waterproofing agents: fatty acids (salts), fatty acid esters, fats and oils, silicones, paraffins, asphalt, waxes, or the like.
(18) Rust preventives: nitrite salts, phosphate salts, zinc oxide, or the like.
(19) Cracking reducing agents: polyoxyalkyl ethers, or the like.
(20) Expansive admixtures: ettringite type, coal-derived type, or the like.

As other conventionally known cement additives (materials), cement wetting agents, thickening agents, separation reducing agents, flocculants, drying shrinkage-reducing agent, strength increasing agents, self-leveling agents, rust-preventing agent, colorants, antifungal agents, and the like can be used. These conventionally known cement additives (materials) can be used either singly or in combination of two or more members.

Particularly preferred embodiments for the components other than cement and water in the cement composition include the followings (1) to (4).

(1) A combination contains essential two components, (i) the cement admixture of the invention and (ii) an oxyalkylene-based antifoaming agent. Formulation ratio by weight of (ii) the oxyalkylene-based antifoaming agent is preferably in the range of 0.001 to 10% by weight relative to the polymer in (i) the cement admixture of the invention.

(2) A combination contains essential two components (i) the cement admixture of the invention and (ii) a material separation reducing agent. As the material separation reducing agent, various thickeners such as nonionic cellulose ethers and compounds having, as partial structure, a hydrophobic substituent group composed of a hydrocarbon chain with carbon atoms of 4 to 30 and a polyoxyalkylene chain added with alkylene oxides of average addition mole number 2 to 300, which have carbon atoms of 2 to 18 can be used. Formulation ratio by weight of the polymer in (i) the cement admixture of the invention and (ii) the material separation reducing agent is preferably in the range of 10/90 to 99.99/0.01, and more preferably 50/50 to 99.9/0.1. A cement composition of this combination is suitable as high flow concrete, self-filling concrete and self-leveling material.

(3) A combination contains essential two components, (i) the cement admixture of the invention and (ii) a sulfonic acid-based dispersing agent having a sulfonic acid group in the molecule. As the sulfonic acid-based dispersing agent, for example, a dispersing agent such as lignin sulfonate salts, condensates of naphthalene sulfonic acid-formalin, condensates of melamine sulfonic acid-formalin, polystyrene sulfonate salts and a aminosulfonic acid-based dispersing agent such as condensates of aminoaryl sulfonic acid-phenol-formaldehyde can be used. Further, formulation ratio by weight of the polymer in (i) the cement admixture of the invention and (ii) the sulfonic acid-based dispersing agent having a sulfonic acid group in the molecule is preferably in the range of 5/95 to 95/5, and more preferably in the range of 10/90 to 90/10.

(4) A combination contains essential two components, (i) the cement admixture of the invention and (ii) lignin sulfonic acid salt. Formulation ratio by weight of the polymer in (i) the cement admixture of the invention and (ii) the lignin sulfonic acid salt is preferably in the range of 5/95 to 95/5, and more preferably in the range of 10/90 to 90/10.

Further, the polymer produced by the production method of the invention can be added to various compositions not only as a cement admixture but also as a paint dispersing agent, a pigment dispersing agent, an anti-static agent, or a thickening agent. When the polymer of the invention is used as a paint dispersing agent, a pigment dispersing agent, an anti-static agent, or a thickening agent, the content in the composition can be suitably adjusted.

EXAMPLES

Hereinafter, the present invention is described in more detail with reference to Examples, but it is not limited to only these Examples. The present invention can be appropriately changed without departing from the above or below-mentioned content. The changed embodiments are also included within the scope of the present invention. Further, in the following production examples, the terms "%" and "ppm" are based on weight, unless otherwise specified. Hereinafter, alkenyl alcohol added with ethylene oxide is referred to as an "adduct of alkenyl alcohol".

<Measurement of Polyethylene Glycol Content>

Content of polyethylene glycol in the monomer composition was measured by gel permeation chromatography (GPC) under the following conditions.

Column for use: GF-1G 7B (guard column) manufactured by Showa Denko K.K. and GF-310HQ manufactured by Showa Denko K.K.

Eluent: water

Flow rate: 1 ml/min

Injection amount: 100 μL, as 5.0% concentration of monomer composition in eluent solution Column temperature: 40° C.

Standard material: polyethylene glycol, peak top molecular weight (Mp) 4020

Detector: Differential refractometer L-7490 manufactured by Hitachi, Ltd.

First, method for measuring the content of the copolymer in the polymer (that is, net amount of polymer) and weight average molecular weight of the copolymer is described.

<Measurement of Weight Average Molecular Weight of Copolymer>

Weight average molecular weight of the copolymer included in the polymer is measured by gel permeation chromatography (GPC) under the following conditions.

Column for use: TSK guard column SWXL, TSKgel G4000SWXL, G3000SWXL, and G2000SWXL manufactured by Tosoh K.K.

Eluent: Eluent solution as a mixture solvent containing 10999 g of water and 6001 g of acetonitrile in which 115.6 g of sodium acetate trihydrate is dissolved and pH is adjusted to 6.0 with acetic acid.

Injection amount: 100 μL, as 0.5% concentration of polymer in eluent solution

Column temperature: 40° C.

Standard material: polyethylene glycol, peak top molecular weight (Mp) 300000, 219300, 107000, 50000, 24000, 11840, 6450, 4020, 1470

Calibration curve order: third-order

Detector: Differential refractometer 410 manufactured by Nihon Waters K.K.

Software for analysis: Empower software manufactured by Nihon Waters K.K.

<Measurement of Content of Copolymer in Polymer (Net Amount of Polymer)>

The obtained polymer was measured by GPC and from the peak areas of the polymer peak and unsaturated polyalkylene glycol ether-based monomer area, the net amount of polymer was calculated based on the following equation.

Net amount of polymer (%)=(Peak area of polymer)×100/(Peak area of polymer+Area of unsaturated polyalkylene glycol ether-based monomer)<

<Preparation of Unsaturated Polyalkylene Glycol Ether>

Production Example 1

10 Mole Adduct of 3-methyl-3-buten-1-ol

To an autoclave reactor made of SUS which is equipped with a thermometer, a stirrer, a tube for introducing raw materials, and a tube for introducing nitrogen, 100 parts of 3-methyl-3-buten-1-ol and 0.3 parts of sodium hydroxide as an alkali catalyst were added. The reaction vessel was purged with nitrogen under stirring, and the mixture was heated to 120° C. under nitrogen atmosphere. While maintained at 120° C. under safe pressure, 505 parts of ethylene oxide were added to the reactor over 8.5 hours. After that, the mixture was aged for 1 hour and the reaction was completed. The obtained reaction product contains unsaturated polyalkylene glycol ether (1) having 3-methyl-3-buten-1-ol added with 10 moles of ethylene oxide on average and polyethylene glycol. This reaction product is referred to as the reaction product (1).

Production Example 1-A

50 Mole Adduct of 3-methyl-3-buten-1-ol

To an autoclave reactor made of SUS which is equipped with a thermometer, a stirrer, a tube for introducing raw materials, and a tube for introducing nitrogen, 100 parts of the reaction product (1) which has been obtained from the Production example 1 and 0.35 parts of 49% aqueous solution of sodium hydroxide as an alkali catalyst were added and the temperature was raised to 95° C. Subsequently, under stifling, a tube equipped with a glass trap was connected to the top of the reaction vessel and pressure inside the reaction vessel was lowered to $5.32 \times 10^3$ Pa (40 Torr) by using a vacuum pump. After completing dehydration for 2.5 hours, the reaction vessel was purged with nitrogen and the temperature was raised to 95° C. under nitrogen atmosphere. Thereafter, while maintained at 95° C. under safe pressure, 339.3 parts of ethylene oxide were added to the reactor over 15.5 hours. After that, the mixture was aged for 1 hour and the reaction was completed. The obtained reaction product contains unsaturated polyalkylene glycol ether-based monomer (I-1) having 3-methyl-3-buten-1-ol added with 50 moles of ethylene oxide on average and polyethylene glycol. This reaction product is referred to as the reaction product (I-1). As a result of analyzing the reaction product (I-1), the amount of polyethylene glycol was found to be 3.8%.

Production Example 1-B

50 Mole Adduct of 3-methyl-3-buten-1-ol

To an autoclave reactor made of SUS which is equipped with a thermometer, a stirrer, a tube for introducing raw materials, and a tube for introducing nitrogen, 100 parts of the reaction product (1) which has been obtained from the Production example 1 and 0.61 parts of 49% aqueous solution of sodium hydroxide as an alkali catalyst were added and the temperature was raised to 95° C. Subsequently, under stirring, a tube equipped with a glass trap was connected to the top of the reaction vessel and pressure inside the reaction vessel was lowered to $5.32 \times 10^3$ Pa (40 Torr) by using a vacuum pump. After completing dehydration for 2.5 hours, the reaction vessel was purged with nitrogen and the temperature was raised to 95° C. under nitrogen atmosphere. Thereafter, while maintained at 95° C. under safe pressure, 339.3 parts of ethylene oxide were added to the reactor over 10.0 hours. After that, the mixture was aged for 1 hour and the reaction was completed. The obtained reaction product contains unsaturated polyalkylene glycol ether-based monomer (I-1) having 3-methyl-3-buten-1-ol added with 50 moles of ethylene oxide on average and polyethylene glycol. This reaction product is referred to as the reaction product (I-2). As a result of analyzing the reaction product (I-2), the amount of polyethylene glycol was found to be 4.0%.

Production Example 1-C

50 Mole Adduct of 3-methyl-3-buten-1-ol

To an autoclave reactor made of SUS which is equipped with a thermometer, a stirrer, a tube for introducing raw materials, and a tube for introducing nitrogen, 100 parts of the reaction product (1) which has been obtained from the Production example 1 and 1.69 parts of 49% aqueous solution of sodium hydroxide as an alkali catalyst were added and the temperature was raised to 95° C. Subsequently, under stirring, a tube equipped with a glass trap was connected to the top of the reaction vessel and pressure inside the reaction vessel was lowered to $5.32 \times 10^3$ Pa (40 Torr) by using a vacuum pump. After completing dehydration for 2.5 hours, the reaction vessel was purged with nitrogen and the temperature was raised to 95° C. under nitrogen atmosphere. Thereafter, while maintained at 95° C. under safe pressure, 339.3 parts of ethylene oxide were added to the reactor over 7.0 hours. After that, the mixture was aged for 1 hour and the reaction was completed. The obtained reaction product contains unsaturated polyalkylene glycol ether-based monomer (1-1) having 3-methyl-3-buten-1-ol added with 50 moles of ethylene oxide on average and polyethylene glycol. This reaction product is referred to as the reaction product (1-3). As a result of analyzing the reaction product (1-3), the amount of polyethylene glycol was found to be 4.7%.

Production Example 2

10 mole adduct of 2-methyl-2-propen-1-ol

To an autoclave reactor made of SUS which is equipped with a thermometer, a stirrer, a tube for introducing raw materials, and a tube for introducing nitrogen, 100 parts of 2-methyl-2-propen-1-ol and 0.07 parts of sodium hydroxide as catalyst for addition reaction were added. The reaction vessel was purged with nitrogen under stirring, and the mixture was heated to 110° C. under nitrogen atmosphere. While maintained at 110° C. under safe pressure, 609.6 parts of ethylene oxide were added to the reactor. After that, the same temperature was maintained until the alkylene oxide addition reaction is completed, and then the reaction was terminated. The obtained reaction product contains unsaturated polyalkylene glycol ether-based monomer (2) having 2-methyl-2-propen-1-ol added with 10 moles of ethylene oxide on average. This reaction product is referred to as the reaction product (2).

Production Example 3

50 Mole Adduct of 2-methyl-2-propen-1-ol

To an autoclave reactor made of SUS which is equipped with a thermometer, a stirrer, a tube for introducing raw materials, and a tube for introducing nitrogen, 100 parts of the reaction product (2) which has been obtained from the Production example 2 and 0.35 parts of 48% aqueous solution of sodium hydroxide as a catalyst for addition reaction were added. After purging the inside of the reaction vessel with nitrogen under stirring, the temperature was raised to 100° C. Subsequently, under stifling, a tube equipped with a glass trap was connected to the top of the reaction vessel and pressure inside the reaction vessel was lowered to $6.65 \times 10^3$ Pa (50 Torr) by using a vacuum pump. After that, while cooling the glass trap using ethanol and dry ice bath, dehydration was performed for 1 hour at the same temperature. Once the dehydration is completed, the temperature was raised to 110° C. under nitrogen atmosphere. Thereafter, while maintained at 110° C. under safe pressure, 339.3 parts of ethylene oxide were added to the reactor and the reaction was completed by maintaining the same temperature until the alkylene oxide addition reaction is completed. The obtained reaction product contains unsaturated polyalkylene glycol ether-based monomer (3) having 2-methyl-2-propen-1-ol added with 50 moles of ethylene oxide on average. This reaction product is referred to as the reaction product (3).

Production Example 3-A 120 mole adduct of 2-methyl-2-propen-1-ol

To an autoclave reactor made of SUS which is equipped with a thermometer, a stirrer, a tube for introducing raw materials, and a tube for introducing nitrogen, 100 parts of the reaction product (3) which has been obtained from the Production example 3 and 0.16 parts of 48% aqueous solution of sodium hydroxide as a catalyst for addition reaction were added. After purging the inside of the reaction vessel with nitrogen under stirring, the temperature was raised to 100° C. Subsequently, under stirring, a tube equipped with a glass trap was connected to the top of the reaction vessel and pressure inside the reaction vessel was lowered to $6.65 \times 10^3$ Pa (50 Torr) by using a vacuum pump. After that, while cooling the glass trap using ethanol and dry ice bath, dehydration was performed for 1 hour at the same temperature. After completing dehydration, while maintained at 110° C. under safe pressure, 135.5 parts of ethylene oxide were added to the reactor over 15 hours. After aging the mixture for 1 hour, the reaction was completed. The obtained reaction product contains unsaturated polyalkylene glycol ether-based monomer (4) having 2-methyl-2-propen-1-ol added with 120 moles of ethylene oxide on average. This reaction product is referred to as the reaction product (II-1). As a result of analyzing the reaction product (II-1), the amount of polyethylene glycol was found to be 1.8%.

Production Example 3-B 120 mole adduct of 2-methyl-2-propen-1-ol

To an autoclave reactor made of SUS which is equipped with a thermometer, a stirrer, a tube for introducing raw materials, and a tube for introducing nitrogen, 3821 g of the reaction product (3) which has been obtained from the Production example 3 and 11.83 g of 48% aqueous solution of sodium hydroxide as a catalyst for addition reaction were added. After purging the inside of the reaction vessel with nitrogen under stirring, the temperature was raised to 100° C. Subsequently, under stirring, a tube equipped with a glass trap was connected to the top of the reaction vessel and pressure inside the reaction vessel was lowered to $6.65 \times 10^3$ Pa (50 Torr) by using a vacuum pump. After that, while cooling the glass trap using ethanol and dry ice bath, dehydration was performed for 1 hour at the same temperature. After completing dehydration, while maintained at 110° C. under safe pressure, 5179 g of ethylene oxide were added to the reactor over 10 hours. After aging the mixture for 1 hour, the reaction was completed. The obtained reaction product contains unsaturated polyalkylene glycol ether-based monomer (5) having 2-methyl-2-propen-1-ol added with 120 moles of ethylene oxide on average. This reaction product is referred to as the reaction product (II-2). As a result of analyzing the reaction product (II-2), the amount of polyethylene glycol was found to be 2.0%.

<Storage Stability Test for Aqueous Solution>

Next, the aqueous solution (monomer composition) of the Reference examples 1 to 5, Examples 1 to 6, and Comparative examples 1 to 4 obtained according to the following order was added in a polypropylene container, purged with nitrogen, sealed, and stored in an incubator at 50° C. One day, three days, seven days, or ten days after storage, state of the storage solution (monomer composition) was evaluated with visual observation according to the following evaluation criteria.

Homogeneously transparent: storage solution (monomer composition) is homogeneously transparent Homogeneously turbid: storage solution (monomer composition) is homogeneously turbid With precipitates: storage solution (monomer composition) has formed precipitates <Concentration Adjustment>

For the Reference examples 1 to 5, the reaction product was added with water at 60° C. according to the following order, concentration adjustment was performed, and then the storage stability test was carried out.

Reference Example 1

Adduct of 3-methyl-3-buten-1-ol

In order to lower the softening point and have the storage temperature lower than 60° C., 25 parts of water were added to 100 parts of the reaction product (I-1), and the concentration was adjusted to 80% to give the aqueous solution (I-1). pH of the aqueous solution (I-1) was 13 or higher. In the aqueous solution (I-1), amount of the alkali catalyst was 400 ppm and the amount of alkali metal ion ($Na^+$) was 230 ppm.

Storage stability of the aqueous solution (I-1) was as follows. One day after storage: homogeneously transparent, three days after storage: homogeneously transparent, seven days after storage: homogeneously transparent, and ten days after storage: homogeneously turbid.

Reference Example 2

Adduct of 3-methyl-3-buten-1-ol

In order to lower the softening point and have the storage temperature lower than 60° C., 25 parts of water were added to 100 parts of the reaction product (I-2), and the concentration was adjusted to 80% to give the aqueous solution (I-2). pH of the aqueous solution (I-2) was 13 or higher. In the aqueous solution (I-2), amount of the alkali catalyst was 640 ppm and the amount of alkali metal ion ($Na^+$) was 370 ppm.

Storage stability of the aqueous solution (I-2) was as follows. One day after storage: homogeneously turbid, three days after storage: homogeneously turbid, seven days after storage: with precipitates, and ten days after storage: with precipitates.

Reference Example 3

Adduct of 3-methyl-3-buten-1-ol

In order to lower the softening point and have the storage temperature lower than 60° C., 25 parts of water were added to 100 parts of the reaction product (I-3), and the concentration was adjusted to 80% to give the aqueous solution (I-3). pH of the aqueous solution (I-3) was 13 or higher. In the aqueous solution (I-3), amount of the alkali catalyst was 1600 ppm and the amount of alkali metal ion ($Na^+$) was 920 ppm.

Storage stability of the aqueous solution (I-3) was as follows. One day after storage: homogeneously turbid, three days after storage: with precipitates, seven days after storage: with precipitates, and ten days after storage: with precipitates.

Reference Example 4

Adduct of 2-methyl-2-propen-1-ol

In order to lower the softening point and have the storage temperature lower than 60° C., 25 parts of water were added to 100 parts of the reaction product (II-1), and the concentration was adjusted to 80% to give the aqueous solution (II-1). pH of the aqueous solution (II-1) was 13 or higher. In the aqueous solution (II-1), amount of the alkali catalyst was 400 ppm and the amount of alkali metal ion ($Na^+$) was 230 ppm.

Storage stability of the aqueous solution (II-1) was as follows. One day after storage: homogeneously transparent, three days after storage: homogeneously transparent, seven days after storage: homogeneously transparent, and ten days after storage: homogeneously turbid.

Reference Example 5

Adduct of 2-methyl-2-propen-1-ol

In order to lower the softening point and have the storage temperature lower than 60° C., 25 parts of water were added to 100 parts of the reaction product (II-2), and the concentration was adjusted to 80% to give the aqueous solution (II-2). pH of the aqueous solution (II-2) was 13 or higher. In the aqueous solution (II-2), amount of the alkali catalyst was 640 ppm and the amount of alkali metal ion ($Na^+$) was 370 ppm.

Storage stability of the aqueous solution (II-2) was as follows. One day after storage: homogeneously turbid, three days after storage: homogeneously turbid, seven days after storage: with precipitates, and ten days after storage: with precipitates.

<Concentration Adjustment and Neutralization Treatment>

For the Examples 1 to 6 and Comparative examples 1 to 4, the reaction product was added with water at 60° C. according to the following order and added and mixed with each organic acid at 55° C., concentration adjustment and neutralization treatment were performed, and then the storage stability test was carried out for an aqueous solution.

Comparative Example 1

Adduct of 3-methyl-3-buten-1-ol, Neutralization with Sulfuric Acid

To 100 parts of the reaction product (1-3), 25 parts of water and 0.12 parts of sulfuric acid were added, and the concentration was adjusted to 80% to give the aqueous solution (III-1) with pH of 8.3. In the aqueous solution (III-1), amount of the alkali catalyst was 1600 ppm and the amount of alkali metal ion ($Na^+$) was 920 ppm.

Storage stability of the aqueous solution (III-1) was as follows. One day after storage: with precipitates, three days after storage: with precipitates, seven days after storage: with precipitates, and ten days after storage: with precipitates.

Comparative Example 2

Adduct of 3-methyl-3-buten-1-ol, Neutralization with Phosphoric Acid

To 100 parts of the reaction product (I-3), 25 parts of water and 0.15 parts of phosphoric acid were added, and the concentration was adjusted to 80% to give the aqueous solution (III-2) with pH of 11.7. In the aqueous solution (III-2), amount of the alkali catalyst was 1600 ppm and the amount of alkali metal ion ($Na^+$) was 920 ppm.

Storage stability of the aqueous solution (III-2) was as follows. One day after storage: with precipitates, three days after storage: with precipitates, seven days after storage: with precipitates, and ten days after storage: with precipitates.

Example 1

Adduct of 3-methyl-3-buten-1-ol, neutralization with Acetic Acid

To 100 parts of the reaction product (I-3), 25 parts of water and 0.67 parts of p-toluene sulfonic acid monohydrate (PTS) were added, and the concentration was adjusted to 80% to give the aqueous solution (III-3) with pH of 8.6. In the aqueous solution (III-3), amount of the alkali catalyst was 1600 ppm and the amount of alkali metal ion ($Na^+$) was 920 ppm.

Storage stability of the aqueous solution (III-3) was as follows. One day after storage: homogeneously transparent, three days after storage: homogeneously transparent, seven days after storage: homogeneously transparent, and ten days after storage: homogeneously transparent.

Example 2

Adduct of 3-methyl-3-buten-1-ol, neutralization with acetic acid

To 100 parts of the reaction product (I-3), 25 parts of water and 0.67 parts of acetic acid were added, and the concentration was adjusted to 80% to give the aqueous solution (III-4) with pH of 7.1. In the aqueous solution (III-4), amount of the alkali catalyst was 1600 ppm and the amount of alkali metal ion ($Na^+$) was 920 ppm.

Storage stability of the aqueous solution (III-4) was as follows. One day after storage: homogeneously transparent, three days after storage: homogeneously transparent, seven days after storage: homogeneously transparent, and ten days after storage: homogeneously transparent.

Example 3

Adduct of 3-methyl-3-buten-1-ol, neutralization with lactic acid

To 100 parts of the reaction product (I-3), 25 parts of water and 1.12 parts of 50% lactic acid were added, and the concentration was adjusted to 80% to give the aqueous solution (III-5) with pH of 7.8. In the aqueous solution (III-5), amount of the alkali catalyst was 1600 ppm and the amount of alkali metal ion ($Na^+$) was 920 ppm.

Storage stability of the aqueous solution (III-5) was as follows. One day after storage: homogeneously transparent, three days after storage: homogeneously transparent, seven days after storage: homogeneously transparent, and ten days after storage: homogeneously transparent.

Comparative Example 3

Adduct of 2-methyl-2-propen-1-ol, Neutralization with Sulfuric Acid

To 100 parts of the reaction product (II-2), 25 parts of water and 0.5 parts of sulfuric acid were added, and the concentration was adjusted to 80% to give the aqueous solution (III-6) with pH of 8.0. In the aqueous solution (III-6), amount of the alkali catalyst was 640 ppm and the amount of alkali metal ion ($Na^+$) was 370 ppm.

Storage stability of the aqueous solution (III-6) was as follows. One day after storage: with precipitates, three days after storage: with precipitates, seven days after storage: with precipitates, and ten days after storage: with precipitates.

Example 4

Adduct of 2-methyl-2-propen-1-ol, neutralization with acetic acid

To 100 parts of the reaction product (II-2), 25 parts of water and 0.27 parts of acetic acid were added to give the aqueous solution (III-7) with pH of 7.5. In the aqueous solution (III-7), amount of the alkali catalyst was 640 ppm and the amount of alkali metal ion ($Na^+$) was 370 ppm.

Storage stability of the aqueous solution (III-7) was as follows. One day after storage: homogeneously transparent, three days after storage: homogeneously transparent, seven days after storage: homogeneously transparent, and ten days after storage: homogeneously transparent.

Example 5

Adduct of 3-methyl-3-buten-1-ol, neutralization with Acetic Acid

To 100 parts of the reaction product (I-1), 25 parts of water and 0.14 parts of p-toluene sulfonic acid monohydrate (PTS) were added, and the concentration was adjusted to 80% to give the aqueous solution (III-8) with pH of 11.2. In the aqueous solution (III-8), amount of the alkali catalyst was 400 ppm and the amount of alkali metal ion ($Na^+$) was 230 ppm.

Storage stability of the aqueous solution (III-8) was as follows. One day after storage: homogeneously transparent, three days after storage: homogeneously transparent, seven days after storage: homogeneously transparent, and ten days after storage: homogeneously transparent.

Comparative Example 4

Adduct of 3-methyl-3-buten-1-ol, neutralization with Acetic Acid

To 100 parts of the reaction product (I-1), 25 parts of water and 0.26 parts of p-toluene sulfonic acid monohydrate (PTS) were added, and the concentration was adjusted to 80% to give the aqueous solution (III-9) with pH of 3.4. In the aqueous solution (III-9), amount of the alkali catalyst was 400 ppm and the amount of alkali metal ion ($Na^+$) was 230 ppm.

Storage stability of the aqueous solution (III-9) was as follows. One day after storage: homogeneously transparent, three days after storage: homogeneously transparent, seven days after storage: homogeneously transparent, and ten days after storage: homogeneously transparent.

Example 6

Adduct of 3-methyl-3-buten-1-ol, neutralization with Acetic Acid

To 100 parts of the reaction product (I-1), 25 parts of water and 0.17 parts of acetic acid were added, and the concentration was adjusted to 80% to give the aqueous solution (III-10) with pH of 4.5. In the aqueous solution (III-10), amount of the alkali catalyst was 400 ppm and the amount of alkali metal ion (Na+) was 230 ppm.

Storage stability of the aqueous solution (III-10) was as follows. One day after storage: homogeneously transparent, three days after storage: homogeneously transparent, seven days after storage: homogeneously transparent, and ten days after storage: homogeneously transparent.

Next, by using the monomer composition (aqueous solution) obtained, the polymer was produced and subjected to the following evaluations.

<Determination of Influence of Monomer Composition Stability on Polymerization>

By using the 50° C. storage solution used for the above-described storage stability test (50° C., stored for 7 days), a polymer was prepared and influence of the stability of monomer composition on polymerization was determined.

<Concrete Test>

The obtained polymer was subjected to a cement admixture performance test by using it as a cement admixture. The evaluation processes are as follows.

Namely, each component was weighed to have kneading amount of 30 L. The raw concrete materials, blending, and kneading method are described below. Then, the components were kneaded by using a pan type mixer. By using the polymer obtained from the aqueous solutions III-2, III-3, and III-5, amount of the admixture to have a predetermined slump flow value and the slump flow value right after kneading were evaluated. The addition amount of the cement admixture relative to the weight of cement was calculated based on non-volatile components in the admixture and expressed as % by weight in the table. Further, if necessary, 0.1% by weight aqueous solution of MA404 (trade name, manufactured by Pozzolith Bussan Co., Ltd.) was added by itself as an antifoaming agent, and the air amount was adjusted to less than 1%.

<Raw Materials for Use>

As for the cement, common Portland cement (specific gravity: 3.16) manufactured by Taiheiyo Cement Corporation was evenly mixed and used. Crushed stones from Ome were used as coarse aggregate, and sand from Kakegawa and mountain sand from Kimitsu were admixed at the ratio of 8/2 and used as fine aggregate. As for the water for kneading, tap water was used.

<Concrete Formulation>

Unit amount of cement: 573.0 Kg/m³
Unit amount of water: 172.0 Kg/m³ (including polymer and admixture such as AE)
Unit amount of fine aggregate: 866.0 Kg/m³
Unit amount of coarse aggregate: 744.0 Kg/m³
Water-cement ratio (W/C):30.0%
Ratio of fine aggregate (s/a):47.0%

<Kneading of Materials>

Cement and fine aggregate were added to a mixer and kneaded for 10 sec. After stopping the kneading, a predetermined amount of water and admixture was added to the mixer immediately followed by kneading for 40 sec. Then, coarse aggregate was added and kneaded again for 90 sec. Fresh concrete obtained after completing the kneading was discharged and subjected to an evaluation test. Meanwhile, for the evaluation test, the kneading start time after adding water and admixture was taken as 0 min.

<Evaluation of Fresh Concrete>

The obtained fresh concrete was subjected to a slump flow value measurement according to the following method.

Slump flow value: JIS A 1101-1998

<Use Amount of Polymer Obtained from Aqueous Solution>

The amount of 0.155% by weight (solid content basis) was added uniformly per cement amount.

Comparative Example 5

To a glass reaction vessel equipped with a thermometer, a stirrer, a dropping funnel, a nitrogen introducing tube, and a condenser, 25.8 parts of water, 100 parts of the top layer of storage solution of the aqueous solution (III-2) (Comparative example 2), which does not contain a separated layer of that, as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 35000) was 89.1%, excluding the amount of GPC (gel permeation chromatography) peak corresponding to the monomer (Mw 2200).

Further, the concrete test was carried out for the obtained polymer. As a result, the slump flow value right after kneading was found to be 545 mm.

Comparative Example 6

To a glass reaction vessel equipped with a thermometer, a stirrer, a dropping funnel, a nitrogen introducing tube, and a condenser, 25.8 parts of water, 100 parts of the bottom layer of storage solution of the aqueous solution (III-2) (Comparative example 2), which contains a separated layer of that, as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 g of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 32000) was 83.2%, excluding the amount of the GPC (gel permeation chromatography) peak corresponding to the monomer (Mw 2200).

Further, the concrete test was carried out for the obtained polymer. As a result, the slump flow value right after kneading was found to be 425 mm.

Example 7

To a glass reaction vessel equipped with a thermometer, a stirrer, a dropping funnel, a nitrogen introducing tube, and a condenser, 25.8 parts of water, 100 parts of the top layer of storage solution of the aqueous solution (III-3) (Example 1), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 35000) was 88.9%, excluding the amount of the GPC (gel permeation chromatography) peak corresponding to the monomer (Mw 2200).

Further, the concrete test was carried out for the obtained polymer. As a result, the slump flow value right after kneading was found to be 515 mm.

Example 8

To a glass reaction vessel equipped with a thermometer, a stirrer, a dropping funnel, a nitrogen introducing tube, and a condenser, 25.8 parts of water, 100 parts of the bottom layer of storage solution of the aqueous solution (III-3) (Example 1), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 35000) was 89.2%, excluding the amount of the GPC (gel permeation chromatography) peak corresponding to the monomer (Mw 2200).

Further, the concrete test was carried out for the obtained polymer. As a result, the slump flow value right after kneading was found to be 540 mm.

Example 9

To a glass reaction vessel equipped with a thermometer, a stirrer, a dropping funnel, a nitrogen introducing tube, and a condenser, 25.8 parts of water, 100 parts of the top layer of storage solution of the aqueous solution (III-5) (Example 3), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH Net amount of the polymer (Mw 36000) was 89.5%, excluding the amount of the GPC (gel permeation chromatography) peak corresponding to the monomer (Mw 2200).

Further, the concrete test was carried out for the obtained polymer. As a result, the slump flow value right after kneading was found to be 565 mm.

Example 10

To a glass reaction vessel equipped with a thermometer, a stirrer, a dropping funnel, a nitrogen introducing tube, and a condenser, 25.8 parts of water, 100 parts of the bottom layer of storage solution of the aqueous solution (III-5) (Example 3), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 36000) was 89.3%, excluding the amount of the GPC (gel permeation chromatography) peak corresponding to the monomer (Mw 2200).

Further, the concrete test was carried out for the obtained polymer. As a result, the slump flow value right after kneading was found to be 538 mm.

Example 11

To a glass reaction vessel equipped with a thermometer, a stirrer, a dropping funnel, a nitrogen introducing tube, and a condenser, 25.8 parts of water, 100 parts of the aqueous solution (III-8) (Example 5), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 34500) was 89.0%, excluding the amount of the GPC (gel permeation chromatography) peak corresponding to the monomer (Mw 2200).

Further, the concrete test was carried out for the obtained polymer. As a result, the slump flow value right after kneading was found to be 545 mm.

Comparative Example 7

To a glass reaction vessel equipped with a thermometer, a stirrer, a dropping funnel, a nitrogen introducing tube, and a condenser, 25.8 parts of water, 100 parts of the aqueous solution (III-9) (Comparative example 4), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 23000) was 63.2%, excluding the amount of the GPC (gel permeation chromatography) peak corresponding to the monomer (Mw 2200).

Further, the concrete test was carried out for the obtained polymer. As a result, the slump flow value right after kneading was found to be 310 mm.

Example 12

To a glass reaction vessel equipped with a thermometer, a stirrer, a dropping funnel, a nitrogen introducing tube, and a condenser, 25.8 parts of water, 100 parts of the aqueous solution (III-10) (Example 6), as a monomer of unsaturated polyalkylene glycol ether, and 0.15 parts of acrylic acid were added. The reaction vessel was purged with nitrogen under stirring. After increasing the temperature to 58° C. under nitrogen atmosphere, 6.3 parts of 2% aqueous solution of hydrogen peroxide was added. Once the temperature was stabilized at 58° C., an aqueous solution of unsaturated carboxylic acid monomer in which 10.7 parts of acrylic acid was dissolved in 5.2 parts of water was added dropwise thereto over 3 hours. At the same time adding dropwise the aqueous acrylic acid solution, an aqueous solution in which 0.16 parts of L-ascorbic acid and 0.35 parts of 2-mercaptopropionic acid were dissolved in 9.8 parts of water was added dropwise thereto over 3.5 hours. Thereafter, by maintaining for 1 hour at 58° C., it was allowed to complete the polymerization reaction. After cooling, it was neutralized to pH 6.5 using 49% NaOH. Net amount of the polymer (Mw 35500) was 89.5%, excluding the amount of the GPC (gel permeation chromatography) peak corresponding to the monomer (Mw 2200).

Further, the concrete test was carried out for the obtained polymer. As a result, the slump flow value right after kneading was found to be 530 mm.

The invention claimed is:

1. A method for producing the monomer composition, the method comprising:
    a reaction step for reacting alkenyl alcohol with alkylene oxide having 2 to 18 carbon atoms in the presence of an alkali catalyst to give an unsaturated polyalkylene glycol ether-based monomer, said alkenyl alcohol; selected from the groups consisting of 3-methyl-3-buten-1-ol ($CH_2$=$C(CH_3)$—$CH_2CH_2$—OH), 2-methyl-3-buten-1-ol ($CH_2$=$CHCH(CH_3)$—$CH_2$—OH), 5-hexen-1-ol ($CH_2$=$CHCH_2CH_2CH_2CH_2$—OH), and 3-hepten-1-ol ($CH_2CH_2CH_2CH$=$CHCH_2CH_2$—OH);
    a concentration adjustment step for adding water to the reaction liquid obtained from the reaction step to yield an aqueous solution: and
    a neutralization step for neutralizing the reaction liquid obtained from the reaction step to pH 4 to pH 13 by using an organic acid, wherein the organic acid is a hydrocarbon having 1 to 10 carbon atoms and has a carboxy group or a sulfo group.

2. A method for producing a polycarboxylic acid-based polymer, the method comprising:
    a reaction step for reacting alkenyl alcohol with alkylene oxide having 2 to 18 carbon atoms in the presence of an alkali catalyst to give an unsaturated polyalkylene glycol ether-based monomer, said alkenyl alcohol selected from the group consisting of 3-methyl-3-buten-1-ol ($CH_2$=$C(CH_3)$—$CH_2CH_2$—OH), 2-methyl-3-buten-1-ol ($CH_2$=$CHCH(CH_3)$—$CH_2$—OH), 5-hexen-1-ol ($CH_2$=$CHCH_2CH_2CH_2CH_2$—OH), and 3-hepten-1-ol ($CH_3CH_2CH_2CH$=$CHCH_2CH_2$—OH);
    a concentration adjustment step for adding water to the reaction liquid obtained from the reaction step to yield an aqueous solution;
    a neutralization step for neutralizing the reaction liquid obtained from the reaction step to pH 4 to pH 13 by using an organic acid, wherein the organic acid is a hydrocarbon having 1 to 10 carbon atoms and has a carboxy group or a sulfo group; and
    a polymerization step for obtaining the polycarboxylic acid-based polymer by using the monomer composition obtained after the neutralization step and reacting the unsaturated polyalkylene glycol ether-based monomer contained in the monomer composition with the unsaturated acid-based monomer represented by the following chemical formula (2):

[Chemical formula 2]

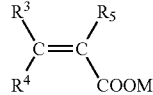

(2)

[in the formula,
    $R^3$, $R^4$, and $R^5$ each independently represent a hydrogen atom, a methyl group, or a —$(CH_2)_p$COOH group (here, p is an integer of from 0 to 2); and
    M represents a hydrogen atom, a metal atom, an ammonium group, or an organic amine group].

3. A method for producing a polycarboxylic acid-based polymer according to claim 2, wherein a time interval between end of the neutralization step and beginning of the polymerization step is 6 hours or more.

4. The method according to claim 2, wherein the organic acid is a hydrocarbon having 1 to 10 carbon atoms which has a sulfo group.

5. The method according to claim 2, wherein the organic acid is selected from the group consisting of acetic acid, phenylacetic acid, phenoxyacetic acid, chloroacetic acid, propionic acid (propane acid), 2-bromopropane acid, 3-phenylpropane acid, lactic acid, butyric acid (butanoic acid), benzoic acid, phthalic acid, terephthalic acid, salicylic acid (2-hydroxybenzoic acid), acetylsalicylic acid (2-acetoxybenzoic acid), citric acid, gluconic acid, methane sulfonic acid, ethane sulfonic acid, benzene sulfonic acid, p-chlorobenzene sulfonic acid, p-toluene sulfonic acid, p-phenol sulfonic acid, and 4-nitrobenzene sulfonic acid.

6. The method according to claim 2, wherein the organic acid is p-toluene sulfonic acid.

7. The method according to claim 2, wherein a content of the organic acid is 0.0001 to 5 parts by weight relative to 100 parts by weight of the monomer.

8. The method according to claim 2, wherein a content of the water is 1 to 50 parts by weight relative to 100 parts by weight of the monomer.

9. The method according to claim 2, wherein an alkali metal ion is included in an amount of 5 to 30,000 ppm by weight.

10. The method according to claim 2, wherein a time interval between end of the neutralization process and start of the polymerization process is 240 hours or more.

11. The method according to claim 2, wherein a temperature of the monomer composition is 50 to 90° C. between end of the neutralization process and start of the polymerization process.

* * * * *